US012653383B2

(12) United States Patent
Chiang et al.

(10) Patent No.: US 12,653,383 B2
(45) Date of Patent: Jun. 16, 2026

(54) BIOLOGICAL BODY IMAGING SYSTEM AND OPTICAL INSPECTION DEVICE

(71) Applicant: ANHUI DENDRITE MEDICAL EQUIPMENT CO., LTD, Hefei (CN)

(72) Inventors: Li-Yang Chiang, Shanghai (CN); Xianjie Weng, Shanghai (CN)

(73) Assignee: ANHUI DENDRITE MEDICAL EQUIPMENT CO., LTD., Hefei (CN)

( * ) Notice: Subject to any disclaimer, the term of this patent is extended or adjusted under 35 U.S.C. 154(b) by 236 days.

(21) Appl. No.: 18/711,185

(22) PCT Filed: Nov. 29, 2023

(86) PCT No.: PCT/CN2023/134948
§ 371 (c)(1),
(2) Date: May 17, 2024

(87) PCT Pub. No.: WO2024/125298
PCT Pub. Date: Jun. 20, 2024

(65) Prior Publication Data
US 2025/0064304 A1 Feb. 27, 2025

(30) Foreign Application Priority Data

Sep. 22, 2023 (CN) .......................... 202311227358.3

(51) Int. Cl.
*A61B 1/00* (2006.01)
*G02B 9/64* (2006.01)
(52) U.S. Cl.
CPC ............ *A61B 1/00188* (2013.01); *G02B 9/64* (2013.01)

(58) Field of Classification Search
CPC .............................. A61B 1/00188; G02B 9/64
USPC .......................................................... 359/362
See application file for complete search history.

(56) References Cited

U.S. PATENT DOCUMENTS

2015/0109671 A1* 4/2015 Kawana ................. G02B 13/18
359/557

* cited by examiner

*Primary Examiner* — Bumsuk Won
*Assistant Examiner* — Mitchell T Oestreich
(74) *Attorney, Agent, or Firm* — Bayramoglu Law Offices LLC

(57) ABSTRACT

The present invention provides a biological body imaging system and an optical inspection device. The biological body imaging system includes a first lens set, a second lens set, a third lens set, and a fourth lens set that all have a positive focal power and are sequentially arranged from an object side along a same optical axis. The first lens set includes a second lens, the second lens set includes a fourth lens and a fifth lens, the third lens set includes a sixth lens, and the fourth lens set includes a seventh lens and an eighth lens. A combined focal length $f_1$ of the first lens set and a conjugate distance T satisfy $0.15 \leq f_1/T \leq 0.18$, a combined focal length $f_4$ of the fourth lens set and the combined focal length $f_1$ of the first lens set satisfy $1.8 \leq f_4/f_1 \leq 2.2$, and a focal length $f_{41}$ of the seventh lens and a focal length $f_{42}$ of the eighth lens satisfy $-1 \leq f_{42}/f_{41} \leq -0.8$. The present invention ensures clarity of the biological body image, especially during long-distance transmission.

11 Claims, 11 Drawing Sheets

10

10

10a

10b

BIOLOGICAL BODY IMAGING SYSTEM AND OPTICAL INSPECTION DEVICE

This application claims priority to Chinese Patent Application No. 20231227358.3, filed with the China National Intellectual Property Administration on Sep. 22, 2023 and entitled "BIOLOGICAL BODY IMAGING SYSTEM AND OPTICAL INSPECTION DEVICE", which is incorporated herein by reference in its entirety.

FIELD OF TECHNOLOGY

The present invention relates to the field of optical technologies, and in particular to, a biological body imaging system and an optical inspection device.

BACKGROUND

An endoscope is a device that examines or treats tissues in the human body using a head probe and optical lenses based on the operation principles of optical imaging and probe technology. With a light source and lenses introduced into body cavities or tissues, microscopic structures or pathological tissues inside the body can be observed. The optical imaging principle of the endoscope means that light of a light source behind the human body enters into the body, and is reflected by an inner wall of an endoscope head and then guided by optical fibers to observation equipment. The optical lens of the endoscope focuses the light, thereby forming an enlarged image for the doctor's observation. Therefore, the quality of the optical imaging directly affects the use effect of the endoscope.

The optical imaging of the endoscope mainly relies on the optical system arranged therein. The optical system is formed by an object lens, a lens set, and an eyepiece arranged sequentially from the front end at which a biological tissue is located to the rear end. The object lens is used to collect information of the biological tissue for imaging, the lens set is used to transmit the image, and the eyepiece is used to enlarge the image for clinical observation by the doctor. The foundation of optical imaging is the biological tissue information collected by the object lens. Therefore, the collection of biological tissue information is an indispensable and crucial part. The quality of the object lens imaging effect depends on many factors, such as the basic imaging performance and imaging aberrations of the object lens. How to ensure the imaging effect of the object lens is a problem to be resolved urgently. In addition, even though the object lens produces a relatively clear image based on the collected biological tissue information, when the lens sets transmit the image, the optical loss due to long-distance transmission in the endoscope is likely to lower the image quality.

In view of this, it is necessary to improve the endoscope in the prior art, so as to resolve the foregoing problem.

SUMMARY

An objective of the present invention is to resolve the problem of poor imaging effect of the object lens in the prior art and the problem of optical loss of the image during long-distance transmission.

To achieve the foregoing objective, according to a first aspect, the present invention provides a biological body imaging system, including:

a first lens set with a positive focal power, a second lens set with a positive focal power, a third lens set with a positive focal power, and a fourth lens set with a positive focal power that are sequentially arranged from an object side along a same optical axis.

The first lens set includes a second lens with a plane facing the object side, the second lens set includes a fourth lens with a convex surface facing the object side and a fifth lens with a convex surface facing an image side that fit with each other, the third lens set includes a sixth lens with a convex surface facing the object side and a concave surface facing the image side, and the fourth lens set includes a seventh lens with a concave surface facing the object side and a convex surface facing the image side and an eighth lens with a convex surface facing the object side and a concave surface facing the image side.

A combined focal length $f_1$ of the first lens set and a conjugate distance T satisfy $0.15 \le f_1/T \le 0.18$, a combined focal length $f_4$ of the fourth lens set and the combined focal length $f_1$ of the first lens set satisfy $1.8 \le f_4/f_1 \le 2.2$, and a focal length $f_{41}$ of the seventh lens and a focal length $f_{42}$ of the eighth lens satisfy $-1 \le f_{42}/f_{41} \le -0.8$.

As further improvement of the present invention, the first lens set further includes a third lens disposed on an image side of the second lens along the same optical axis; and a surface of the third lens facing the image side forms a convex surface.

As further improvement of the present invention, a surface of the third lens facing the object side forms a convex surface or a plane.

As further improvement of the present invention, the first lens set further includes a first lens disposed on an object side of the second lens along the same optical axis and having a plane facing the object side.

As further improvement of the present invention, the first lens fits with the second lens, and surfaces of the first lens on the object side and the image side both form planes.

As further improvement of the present invention, if the surface of the third lens facing the object side forms a convex surface, a curvature radius $r_4$ corresponding to the surface of the third lens facing the object side, an operating distance H of the biological body imaging system, and an air gap $H_1$ between the second lens and the third lens satisfy $4.75 \le r_4/(H+H_1) \le 15.9$.

The operating distance H refers to a distance corresponding to a gap between a central position of the surface of the second lens facing the object side and a biological body, and the air gap $H_1$ refers to a distance corresponding to a gap between a central position of the second lens and a central position of the third lens.

As further improvement of the present invention, the combined focal length $f_1$ of the first lens set and a combined focal length $f_2$ of the second lens set satisfy $7 \le f_2/f_1 \le 11.5$.

As further improvement of the present invention, a combined focal length $f_2$ of the second lens set and a combined focal length $f_3$ of the third lens set satisfy $2.2 \le f_2/f_3 \le 4.5$.

As further improvement of the present invention, a curvature radius $r_3$ corresponding to the surface of the second lens facing the image side and a focal length $f_{12}$ of the second lens satisfy $-0.91 \le r_3/f_{12} \le -0.81$.

As further improvement of the present invention, a curvature radius $r_9$ corresponding to the surface of the sixth lens facing the object side and a combined focal length $f_3$ of the third lens set satisfy $0.15 \le r_9/f_3 \le 0.35$.

As further improvement of the present invention, a curvature radius $r_{12}$ corresponding to the surface of the seventh lens facing the image side and a curvature radius $r_{13}$ corresponding to the surface of the eighth lens facing the object side satisfy $-0.7 \le r_{12}/r_{13} \le -0.5$.

As further improvement of the present invention, a central thickness $D_9$ of the sixth lens and the conjugate distance T satisfy $0.13 \leq D_9/T$.

According to the second aspect, the present invention further provides an optical inspection device.

The optical inspection device includes the biological body imaging system according to any one of descriptions in the first aspect.

Compared with the prior art, the present invention has the following beneficial effects:

The parameter data (for example, numerical aperture, field of view) of the biological body imaging system is controlled using the first lens set, to determine the basic performance of the biological body imaging system. The second lens set is used to correct aberrations, which are mainly spherical aberration, comatic aberration, and chromatic aberration. The third lens set is used to achieve finite conjugate-distance imaging and correct field curvature. The fourth lens set is used to achieve telecentric imaging in the image space, thus ensuring the imaging effect of the biological body imaging system and further guaranteeing clarity of images during long-distance transmission through telecentric imaging in the image space, so as to reduce the optical loss during long-distance transmission.

DESCRIPTION OF THE EMBODIMENTS

The following describes the present invention in detail with reference to implementations shown in the accompanying drawings, but it should be noted that these implementations do not impose limitations on the present invention. Functional, methodological, or structural equivalent transformations or substitutions made by persons of ordinary skill in the art according to these implementations all fall into the protection scope of the present invention.

Figure 1:
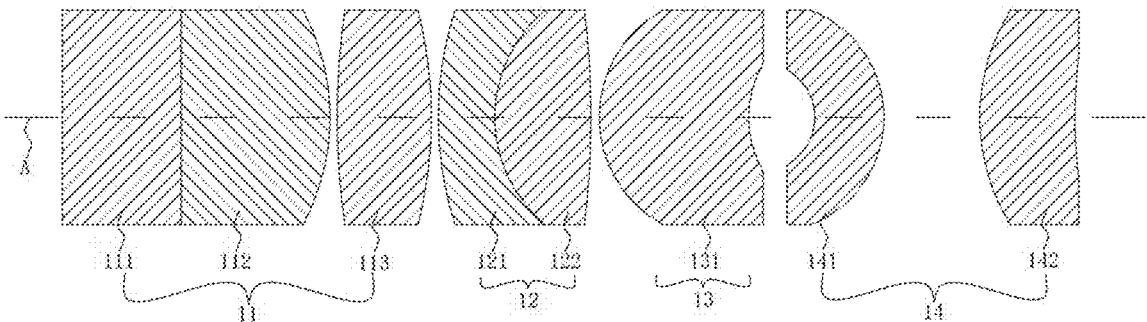
FIG. 1 is a structural cross-sectional view of a biological body imaging system including an optical axis A in a first lens combination manner according to the present invention.
Figure 2:
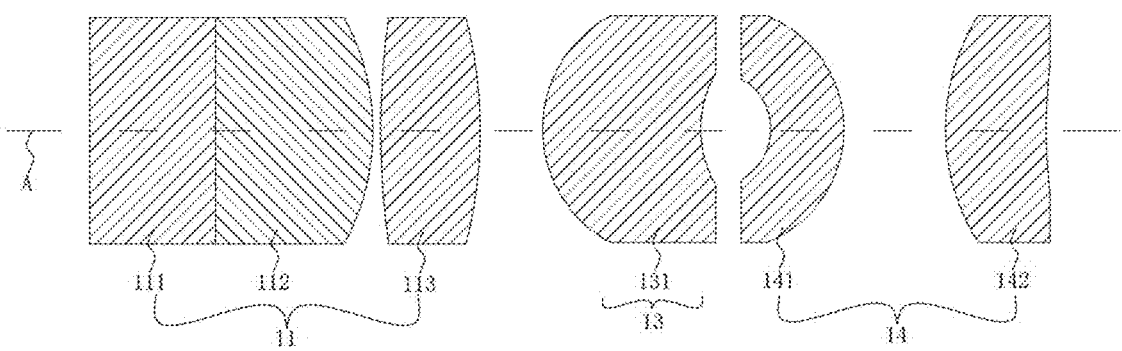
FIG. 2 is a structural cross-sectional view of a biological body imaging system including an optical axis A in a second lens combination manner according to the present invention.
Figure 3:
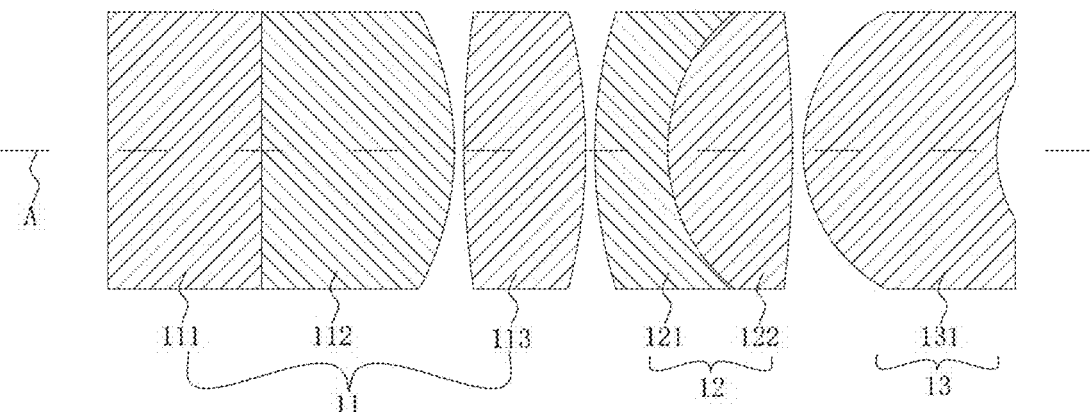
FIG. 3 is a structural cross-sectional view of a biological body imaging system including an optical axis A in a third lens combination manner according to the present invention.

It should be noted that the specific implementations of the present invention are described below in detail with reference to the accompanying drawings. FIG. 1 is a structural cross-sectional view of a biological body imaging system 10 including an optical axis A in a first lens combination manner according to the present invention, where the first lens combination manner means that a first lens set 11, a second lens set 12, a third lens set 13, and a fourth lens set 14 form the biological body imaging system 10; FIG. 2 is a structural cross-sectional view of a biological body imaging system 10a including an optical axis A in a second lens combination manner according to the present invention, where the second lens combination manner means a first lens set 11, a third lens set 13, and a fourth lens set 14 form the biological body imaging system 10a; and FIG. 3 is a structural cross-sectional view of a biological body imaging system 10b including an optical axis A in a third lens combination manner according to the present invention, where the third lens combination manner means a first lens set 11, a second lens set 12, a third lens set 13 form the biological body imaging system 10b. In the perspective shown in FIGS. 1 to 3, the left side is the object side, and the right side is the image side. In addition, for ease of description, the lenses (that is, the first lens 111 to the eighth lens 142) included by biological body imaging systems (that is, the biological body imaging system 10, the biological body imaging system 10*a*, and the biological body imaging system 10*b*) are defined as optical elements. In a practical application scenario (for example, an endoscope described below is used to observe a biological body), before a biological body imaging system is used to image the biological body, an end of the biological body imaging system close to the object side is immersed in normal saline to form a layer of physiological saline at the end.

Further, for ease of description in the following embodiments, in this application, the normal saline can be also defined as an optical element. "MTF" in the "MTF graph" of the present invention stands for modulation transfer function. In the transfer function, the abscissa represents spatial frequency in the unit of cycles per millimeter, and the ordinate represents the image contrast of the corresponding spatial frequency.

Referring to FIGS. 1 to 23, the present invention shows specific implementations of a biological body imaging system. The biological body imaging system is mounted at an optical inspection device for observing a biological body (which includes a living creature or a detached biological tissue), and is specifically mounted at an end of the optical inspection device to optically image the biological body, so as to produce a biological body image for observation by the operator. The optical inspection device may be, for example, an endoscope, which is designed to enter the human body through a natural cavity or a small surgical incision in the body. The biological body imaging system is mounted in a hollow cavity formed at an end of the endoscope, and the endoscope is guided to an organ requiring examination, so as to obtain the corresponding images of the organ requiring examination for observation by the medical personnel. In addition, the applicant points out that the endoscope is specifically used as an example for exemplary description in the following specification. Certainly, the optical inspection device may alternatively be a device used for crack detection in the industrial sector. This is not limited in this embodiment, but does not limit the protection scope of this application. As shown in FIG. 1, the biological body imaging system 10 includes a first lens set 11 with a positive focal power, a second lens set 12 with a positive focal power, a third lens set 13 with a positive focal power, and a fourth lens set 14 with a positive focal power that are sequentially arranged from an object side along the same optical axis (that is, the optical axis A shown in FIG. 1). The first lens set 11 is used for setting parameter data (for example, numerical aperture, field of view) of the biological body imaging system 10, determining the basic performance of the biological body imaging system 10. The second lens set 12 is disposed between the first lens set 11 and the third lens set 13 along the same optical axis to correct aberrations, which are mainly spherical aberration, comatic aberration, and chromatic aberration. The third lens set 13 is configured to achieve finite conjugate-distance imaging and also to correct field curvature. The fourth lens set 14 is configured to achieve telecentric imaging in the image space, thus ensuring the imaging effect of the biological body imaging system 10. Additionally, it can further guarantee clarity of images during long-distance transmission through telecentric imaging in the image space, reducing the optical loss during long-distance transmission.

It should be noted that the telecentric imaging in the image space is to enable a chief ray in each off-axis field of view in the image space to be parallel to the optical axis (or approximately parallel to the optical axis), and non-telecentric imaging in the image space is to enable the chief ray in each off-axis field of view not to be parallel to the optical axis. The chief rays are typically located at the center of the defocused spot corresponding to the field of view in the image space. When the chief ray is on the image plane, the defocused spot is minimized, and when the chief ray is behind the image plane, the defocused spot gradually becomes large. For a telecentric system, behind the image plane, the chief ray is not changed in height and angle, and for a non-telecentric system, the chief ray increases in height and remains unchanged in angle. For the receiving system behind, the telecentric system requires a smaller diameter and deflection angle of the receiving system than the non-telecentric system. It can be therefore seen that telecentric imaging in the image space can keep image clarity unchanged during long-distance transmission.

The first lens set 11 includes a second lens 112 disposed along the optical axis A with a plane facing the object side. A surface of the second lens 112 facing the image side forms a convex surface. Light rays reflected by the surface of the biological body sequentially pass through the plane and the convex surface respectively formed on the object side and the image side of the second lens 112 to be gathered, effectively avoiding the problem that the reflected light rays cannot pass through the second lens set 12 due to the large reflection angle, thus reducing light loss. The surface of the second lens 112 facing the object side may be a convex surface or a plane, and is preferably a plane, so as to prevent or reduce the residual attachment such as liquid on the surface (that is, the surface of the second lens 112 facing the object side) when the biological body imaging system 10 is carried on the optical inspection device for use.

The first lens set 11 further includes a third lens 113 disposed on the image side of the second lens 112 along the same optical axis A. The surface of the third lens 113 facing the image side forms a convex surface. The light rays reflected by the surface of the object are refracted by the second lens 112 to form refracted light rays. The third lens 113 is disposed on the image side of the second lens 112 to perform secondary gathering on the light rays refracted by the second lens 112, further avoiding the problem that the refracted light rays are unable to pass through the second lens set 12 due to a large refraction angle (which is equivalent to the refraction angle formed by the optical axis A), thus reducing the light loss. The surface of the third lens 113 facing the object side forms a convex surface or a plane. When the surface of the third lens 113 facing the object side forms a convex surface, second gathering is performed on the refracted light rays through the convex surface (that is, the surface of the third lens 113 facing the object side), and third gathering is performed on the refracted light rays through the convex surface of the third lens 113 facing the image side, still further avoiding the problem that the refracted light rays are unable to pass through the second lens set 12 due to a large refraction angle, thus reducing the light loss. When the surface of the third lens 113 facing the object side forms a plane, the plane (that is, a plane of the third lens 113 facing the object side) does not gather the refracted light rays, which undergo second gathering only by the convex surface of the third lens 113 facing the image side. This avoids the problem that the refracted light rays are unable to pass through the second lens set 12 due to a large refraction angle, thus reducing light loss. The surface of the third lens 113 facing the object side may be a convex surface or a plane as long as the third lens 113 can gather the light rays refracted by the second lens 112.

The first lens set 11 further includes a first lens 111 disposed on an object side of the second lens 112 along the same optical axis and having a plane facing the object side.

The first lens 111 is disposed on the object side of the second lens 112, that is, at a position in the biological body imaging system 10 closest to the object side, to shield optical elements such as the second lens 112, the third lens 113, and the second lens set 12, thus avoiding scratch on the surface of the second lens 112 facing the object side. In addition, the first lens 111 is arranged as a flat lens, avoiding the change in optical path when the reflected light rays pass through the first lens 111, where due to such change, some or all of the refracted light rays cannot pass through the second lens 112, thus reducing light loss, that is, reducing the interference of the first lens 111 with the optical path of the reflected light rays. In a practical application scenario, the first lens 111 may also be normal saline.

It should be noted that the second lens 112 alone may form a first lens set 11, the second lens 112 and the third lens 113 are combined to form the first lens set 11, the first lens 111 and the second lens 112 are combined to form the first lens set 11, or the first lens 111, the second lens 112, and the third lens 113 are combined to form the first lens set 11. The combination manner of the first lens set 11 is not specifically limited in this embodiment. Any one of the foregoing cases stands as long as the first lens set 11 can gather the light rays reflected by the surface of the biological body surface, such that the parameter data of the biological body imaging system is set, such as the numerical aperture, field of view. In addition, preferably, if the first lens 111, the second lens 112, and the third lens 113 are combined to form the first lens set 11, the first lens 111 is a flat lens, the second lens 112 is a plano-convex lens, and the third lens 113 is a double-convex lens.

In addition, the first lens 111 may fit with the second lens 112 and the surfaces of the first lens 111 on the object side and image side are both planes. The fitting arrangement means that the surface of the first lens 111 facing the image side and the surface of the second lens 112 facing the object side fit into one surface, so as to eliminate refraction losses by two surfaces (that is, the surface of the first lens 111 facing the image side and the surface of the second lens 112 facing the object side) and prevent total refraction in the gap. This further is conducive to mounting the first lens 111 and the second lens 112. Optionally, the gap between the first lens 111 and the second lens 112 may be vacuumed, to reduce the interference of air with refracted light.

The second lens set 12 includes a fourth lens 121 with a convex surface facing the object side and a fifth lens 122 with a convex surface facing the image side that fit with each other along the same optical axis A. The fourth lens 121 has a convex surface facing the object side and a concave surface facing the image side, and the surface of the fifth lens 122 facing the image side and the surface facing the object side are both convex surfaces. The refracted light rays passing through the first lens set 11 sequentially pass through the fourth lens 121 and the fifth lens 122. The fourth lens 121 diverges the refracted light rays passing through the first lens set 11, and the fifth lens 122 gathers the refracted light rays passing through the fourth lens 121, so as to correct spherical aberration, comatic aberration, and chromatic aberration.

The arrangement manner of the fourth lens 121 and the fifth lens 122 may be fitting as described above. That is, the surface of the fourth lens 121 facing the image side fits with the surface of the fifth lens 122 facing the object side, to form the second lens set 12 which has a positive focal power, so as to eliminate refraction losses by two surfaces (that is, the surface of the fourth lens 121 facing the image side and the surface of the fifth lens 122 facing the object side) and prevent total refraction in the gap. This is also conducive to mounting the fourth lens 121 and the fifth lens 122. Certainly, as described above, the gap between the fourth lens 121 and the fifth lens 122 may also be vacuumed to reduce the interference of the gap with refracted light.

The third lens set 13 includes a sixth lens 131 arranged along the same optical axis A. The surface of the sixth lens 131 facing the object side forms a convex surface, and the surface of the sixth lens 131 facing the image side forms a concave surface, such that the convex surface gathers the refracted light rays from the second lens set 12 (or the first lens set 11), and the concave surface diverges refracted light rays from the convex surface, thus achieving finite conjugate-distance imaging and correcting field curvature (that is, curvature of the image field).

The fourth lens set 14 includes a seventh lens 141 and an eighth lens 142 sequentially arranged from the object side along the same optical axis A. The surface of the seventh lens 141 facing the object side forms a concave surface, and the surface facing the image side forms a convex surface. The surface of the eighth lens 142 facing the object side forms a convex surface and the surface facing the image side forms a concave surface. The concave surface of the seventh lens 141 diverges the refracted light rays passing through the third lens set 13, and the convex surface of the seventh lens 141 gathers the refracted light rays. The convex surface of the eighth lens 142 gathers the refracted light rays passing through the seventh lens 141, and the concave surface of the eighth lens 142 diverges the refracted light rays, so as to achieve telecentric imaging in the image space.

It should be noted that as shown in FIG. 1, in this application, the first lens set 11, the second lens set 12, the third lens set 13, and the fourth lens set 14 may form the biological body imaging system 10. The parameter data (for example, numerical aperture, field of view) of the biological body imaging system 10 is controlled using the first lens set 11, to determine the basic performance of the biological body imaging system 10. The second lens set 12 is used to correct aberrations, which are mainly spherical aberration, comatic aberration, and chromatic aberration. The third lens set 13 is used to achieve finite conjugate-distance imaging and correct field curvature. The fourth lens set 14 is used to achieve telecentric imaging in the image space, thus ensuring the imaging effect of the biological body imaging system 10 and further guaranteeing clarity of images during long-distance transmission through telecentric imaging in the image space, so as to reduce the optical loss during long-distance transmission. As shown in FIG. 2, in this application, the first lens set 11, the third lens set 13, and the fourth lens set 14 may alternatively form the biological body imaging system 10a to optically image the biological body with the fourth lens set 14 achieving telecentric imaging in the image space, thus ensuring the imaging effect of the biological body imaging system 10 and further ensuring the image clarity during long-distance transmission through telecentric imaging in the image space, so as to reduce optical loss during long-distance transmission. Referring to FIG. 3, in this application, the first lens set 11, the second lens set 12, and the third lens set 13 may alternatively form the biological body imaging system 10b to optically image the biological body, which is not specifically limited in this embodiment, and the structure shown by the biological body imaging system 10 is preferably used. The second lens set 12 is used to correct aberrations, ensuring clarity of the biological body image, and the fourth lens set 14 is used to achieve telecentric imaging in the image space, further ensuring the clarity of the biological body image during long-distance transmission.

In this implementation, each optical element satisfies the following condition: A combined focal length $f_1$ of the first lens set 11 and the conjugate distance T (that is, the conjugate distance T of the biological body imaging system 10) satisfy $0.15 \le f_1/T \le 0.18$. The combined focal length $f_1$ of the first lens set 11 and the combined focal length $f_2$ of the second lens set 12 satisfy $7 \le f_2/f_1 \le 11.5$. The combined focal length $f_2$ of the second lens set 12 and the combined focal length $f_3$ of the third lens set 13 satisfy $2.2 \le f_2/f_3 \le 4.5$. The combined focal length $f_4$ of the fourth lens set 14 and the combined focal length $f_1$ of the first lens set 11 satisfy $1.8 \le f_4/f_1 \le 2.2$. The focal length $f_{41}$ of the seventh lens 141 and the focal length $f_{42}$ of the eighth lens 142 satisfy $-1 \le f_{42}/f_{41} \le -0.8$. The curvature radius $r_3$ corresponding to the surface of the second lens 112 facing the image side and the focal length $f_{12}$ of the second lens 112 satisfy $-0.91 \le r_3/f_{12} \le -0.81$. The curvature radius $r_9$ corresponding to the convex surface of the sixth lens 131 facing the object side and the combined focal length $f_3$ of the third lens set 13 satisfy $0.15 \le r_9/f_3 \le 0.35$. The curvature radius $r_{12}$ corresponding to the convex surface of the seventh lens 141 facing the image side and the curvature radius $r_{13}$ corresponding to the convex surface of the eighth lens 142 facing the object side satisfy $-0.7 \le r_{12}/r_{13} \le -0.5$. The central thickness $D_9$ of the sixth lens 131 and the conjugate distance T satisfy $0.13 \le D_9/T$. If the surface of the third lens 113 facing the object side forms a convex surface, the curvature radius $r_4$ corresponding to the surface of the third lens 113 facing the object side, the operating distance H of the biological body imaging system 10, and an air gap $H_1$ between the second lens 112 and the third lens 113 satisfy $4.75 \le r_4/(H+H_1) \le 15.9$. The air gap $H_1$ refers to a distance corresponding to a gap between a central position of the second lens 112 and the central position of the third lens 113, and the operating distance H refers to a distance corresponding to a gap between a central position of a surface of the second lens 112 facing the object side and the biological body.

The numeral embodiments of the biological body imaging system 10 in the present invention are described below.

Embodiment 1

The lens structure of a biological body imaging system 10 in Embodiment 1 is shown in FIG. 1. For the method shown in the figure, reference is made to the foregoing description, and repeated description is omitted herein.

The biological body imaging system 10 in Embodiment 1 is formed by sequentially arranging a first lens set 11 with a positive focal power, a second lens set 12 with a positive focal power, a third lens set 13 with a positive focal power, and a fourth lens set 14 with a positive focal power from the object side along the same optical axis (that is, the optical axis A). The first lens set 11 is sequentially formed from the object side by a second lens 112 with a plane facing the object side and the third lens 113 with a convex surface facing the image side without the first lens 111, and immersed in normal saline before specific imaging to form a layer of normal saline on the surface of the second lens 112 facing the object side. The second lens set 12 is sequentially formed along the object side through fitting between a fourth lens 121 with a convex surface facing the object side and a fifth lens 122 with a convex surface facing the image side. The third lens set 13 is formed by a sixth lens 131 with a convex surface facing the object side. The fourth lens set 14 is sequentially formed from the object side by a seventh lens 141 with a concave surface facing the object side and an eighth lens 142 with a convex surface facing the object side. The second lens 112 to the eighth lens 142 are all spherical lenses.

The basic parameter table of the optical elements included by the biological body imaging system 10 in Embodiment 1 shown in Table 1 includes serial number (i), curvature radius $(r_i)$, central thickness $(D_i)$, refractive index $(Nd_i)$, and Abbe number $(vd_j)$. The optical elements refer to the normal saline and the second lens 112 to the eighth lens 142. In the basic parameter table, the column labeled serial number (i) indicates numbering the surfaces of optical elements starting from a surface of an optical element closest to the object side as the first surface to the surface, which is incremented sequentially towards the image side, as the i-th surface (i=1, 2, 3, . . . ). The fitting surfaces of two optical elements are defined as one surface (for example, the fourth lens 121 fits with the fifth lens 122, and the surface of the fourth lens 121 facing the image side and the surface of the fifth lens 122 facing the object side are defined as one surface).

Moreover, the surface of the normal saline facing the image side and the surface of the second lens 112 facing the object side are defined as one surface. The column labeled curvature radius $(r_i)$ represents a curvature radius of an i-th surface, and the symbol of the curvature radius $(r_i)$ is positive when the surface facing the object side protrudes and is negative when the surface facing the image side protrudes. In the column labeled central thickness $(D_i)$, $D_1$ represents a distance (that is, a central thickness of the normal saline) corresponding to a gap between the first surface center position and the second surface center position, $D_2$ represents a distance (that is, a central thickness of the second lens 112) corresponding to a gap between the second surface center position and the third surface center position, and $D_3$ represents a distance (that is, an air gap between the second lens 112 and the third lens 113) corresponding to a gap between the third surface center position and the fourth surface center position. By analog, $D_{13}$ represents a distance corresponding to a gap between the 13th surface center position and the 14th surface center position, and $D_{14}$ represents a distance corresponding to a gap between the 14th surface center position and an image surface formed by the biological body. The column labeled refractive index $(Nd_i)$ represents a refractive index between the i-th surface and the i+1-th surface. $Nd_1$ represents a refractive index (that is, the refractive index of the normal saline) between the first surface and the second surface. $Nd_2$ represents a refractive index (that is, the refractive index of the second lens 112) between the second surface and the third surface. $Nd_3$ represents a refractive index (that is, the refractive index of air between the second lens 112 and the third lens 113) between the third refractive index and the fourth refractive index, . . . , by analog. Abbe number $(vd_j)$ represents the Abbe number of the j-th (j=1, 2, 3, . . . ) optical element, and the Abbe number is recorded at the serial number corresponding to the surface of the optical element facing the object side.

It should be noted that i is specifically defined sequentially from the object side to the image side in the foregoing description. The surface of the normal saline facing the object side is defined as the first surface (that is, i=1). Because the normal saline fits with the second lens 112, the surface of the normal saline facing the image side fits with the surface of the second lens 112 facing the object side, and the two surfaces (that is, the surface of the normal saline facing the image side and the surface of the second lens 112 facing the object side) are defined as one surface, that is, the second surface (that is, i=2). The surface of the second lens 112 facing the image side is defined as the third surface (that is, i=3). The surface of the third lens 113 facing the object side is defined as the fourth surface (that is, i=4), . . . , by analog. j is specifically defined sequentially from the object side to the image side. The normal saline is defined as the first optical element (that is, j=1), and the Abbe number corresponding to the first optical element is filled in the column corresponding to the surface (that is, i=1) of the normal saline facing the object side. The second lens 112 is defined as the second optical element (that is, j=2), and the Abbe number corresponding to the second optical element is filled in the column corresponding to the surface (that is, i=2) of the second lens 112 facing the object side. The third lens 113 is defined as the third optical element (that is, j=3), and the Abbe number corresponding to the third optical element is filled in the column corresponding to the surface (that is, i=4) of the third lens 113 facing the object side, . . . , by analog.

The biological body imaging system 10 in Embodiment 1 has a numerical aperture (NA) of 0.5, a field of view of 0.5 (in the unit of, millimeter, mm) in the object space, telecentricity smaller than 0.2 (in the unit of, degree, °) in the image space, and an operating distance of 0.5 (in the unit of, millimeter, mm). "Millimeter" (abbreviated as "mm") is used as the length unit for the numerical values in Table 1, but used once as an example. The unit may be proportionally enlarged or reduced, allowing for the use of other appropriate units as well. Meanwhile, Table 1 shows the values rounded to numbers with specified decimal places.

TABLE 1

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 0.5 | 1.333044 | 55.794 |
| 2 | ∞ | 2.503 | 1.891899 | 37.134 |
| 3 | −2.562 | 1.624 | 1.0 | |
| 4 | 10.108 | 2.432 | 1.528410 | 76.453 |
| 5 | −5.901 | 0.12 | 1.0 | |
| 6 | 6.446 | 0.949 | 1.854779 | 24.799 |
| 7 | 2.303 | 1.525 | 1.528410 | 76.453 |
| 8 | −11.7 | 0.119 | 1.0 | |
| 9 | 2.704 | 2.5 | 1.755000 | 52.319 |
| 10 | 1.712 | 1.025 | 1.0 | |
| 11 | −0.842 | 1.911 | 1.854779 | 24.799 |
| 12 | −2.331 | 0.12 | 1.0 | |
| 13 | 3.449 | 1.663 | 1.963000 | 24.114 |
| 14 | 12.021 | 1.012 | | |

Table 2 shows calculated values of each optical element in Embodiment 1.

TABLE 2

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $r_4/(H + H_1)$ |
|---|---|---|---|---|---|---|---|---|---|
| 0.155 | 8.63 | 3.69 | 2.04 | −0.83 | −0.9 | 0.32 | −0.68 | 0.14 | 4.76 |

Figure 4:
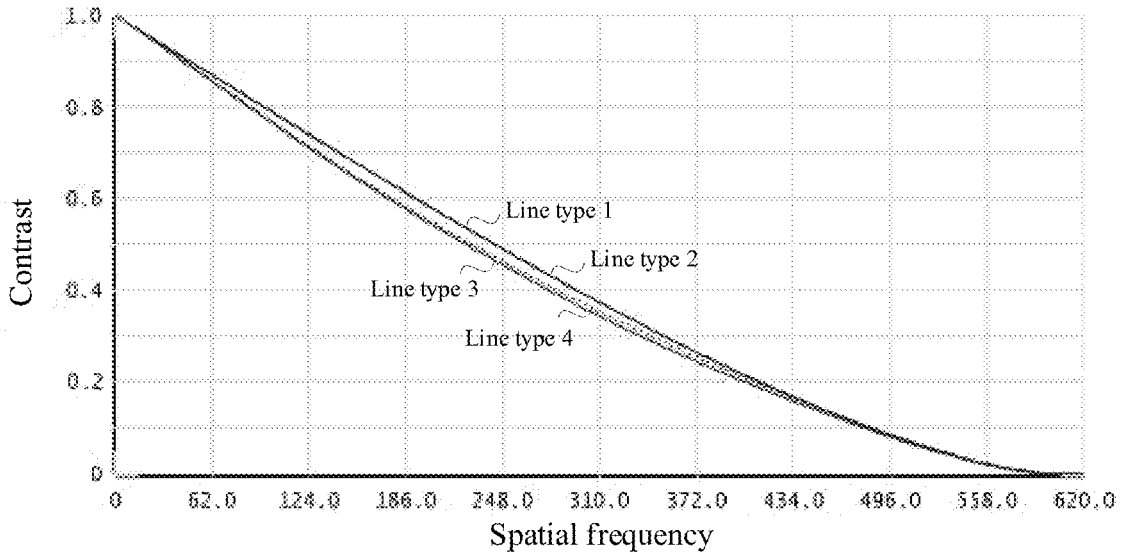
FIG. 4 is an MTF graph of a biological body imaging system at a field of view of 1.0 in a first lens combination manner according to Embodiment 1.
Figure 5:
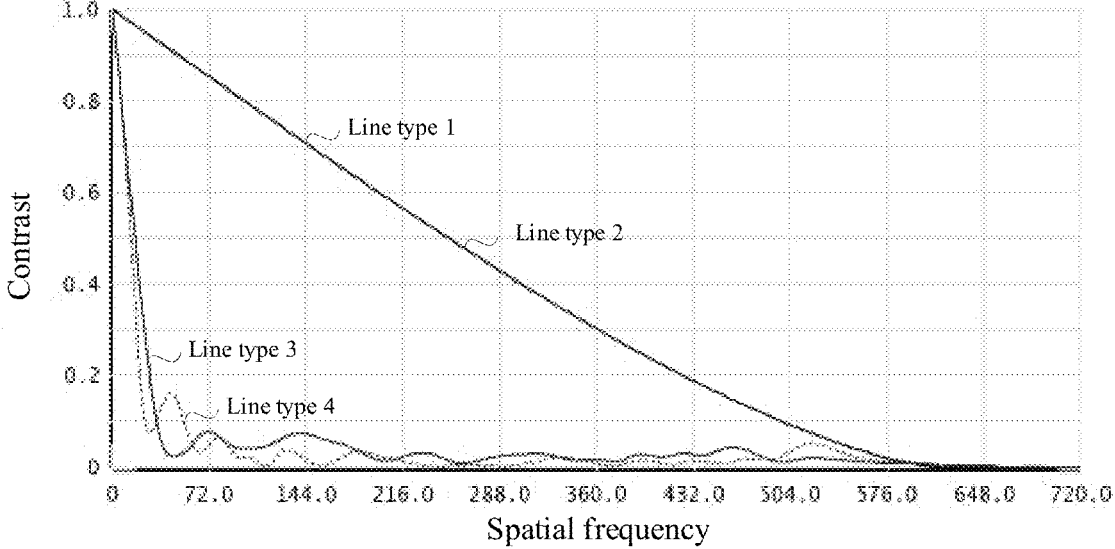
FIG. 5 is an MTF graph of a biological body imaging system at a field of view of 1.0 in a second lens combination manner according to Embodiment 1.
Figure 6:
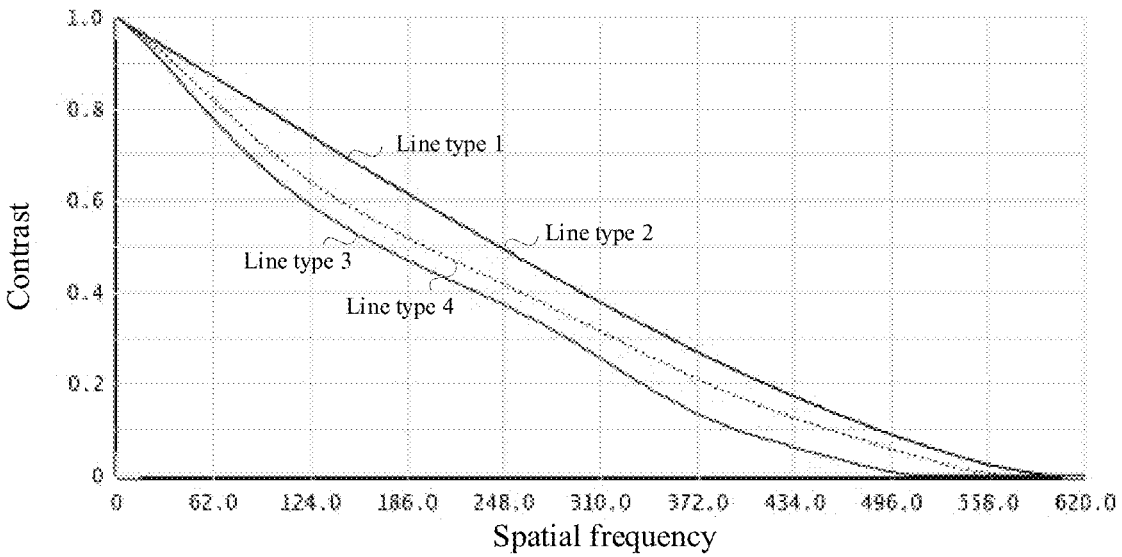
FIG. 6 is an MTF graph of a biological body imaging system at a field of view of 1.0 in a third lens combination manner according to Embodiment 1.

As shown in FIGS. 4 to 6, FIG. 4 is an MTF graph of a biological body imaging system 10 (that is, which is formed by a first lens set 11, a second lens set 12, a third lens set 13, and a fourth lens set 14) at a field of view of 1.0 according to Embodiment 1; FIG. 5 is an MTF graph of a biological body imaging system 10a (that is, which is formed by a first lens set 11, a third lens set 13, and a fourth lens set 14) at a field of view of 1.0 according to Embodiment 1; and FIG. 6 is an MTF graph of a biological body imaging system 10b

(that is, which is formed by a first lens set 11, a second lens set 12, and a third lens set 13) at a field of view of 1.0 according to Embodiment 1.

The abscissa in FIG. 4 represents spatial frequency in the unit of cycles per millimeter (cycles/mm). In FIG. 4, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988823, 0.977607, 0.966306, 0.954857, 0.943218, 0.931446, 0.919606, 0.907723, 0.895815, 0.883894, 0.871974, 0.860067, 0.848184, 0.836321, 0.824479, 0.812669, 0.800896, 0.789156, 0.77745, 0.765788, 0.754175, 0.742606, 0.731084, 0.719625, 0.708231, 0.696881, 0.685578, 0.674352, 0.66327, 0.652425, 0.641792, 0.631215, 0.620642, 0.610128, 0.599697, 0.589337, 0.579027, 0.568738, 0.558492, 0.54835, 0.538362, 0.528566, 0.518897, 0.509231, 0.499553, 0.489911, 0.480318, 0.470768, 0.461231, 0.451676, 0.442163, 0.43278, 0.423547, 0.414444, 0.405416, 0.3964, 0.38737, 0.378332, 0.369378, 0.360603, 0.351959, 0.34338, 0.334903, 0.326574, 0.318381, 0.310292, 0.302268, 0.294265, 0.286253, 0.278243, 0.270358, 0.262673, 0.255074, 0.247489, 0.240026, 0.232737, 0.225502, 0.218265, 0.211146, 0.204185, 0.197247, 0.190284, 0.183432, 0.176724, 0.170008, 0.16325, 0.156603, 0.15009, 0.143546, 0.136956, 0.130489, 0.124154, 0.117776, 0.111362, 0.10511, 0.098996, 0.092797, 0.086605, 0.080767, 0.075238, 0.069677, 0.064096, 0.058738, 0.053541, 0.048263, 0.043071, 0.038322, 0.033842, 0.029222, 0.024744, 0.020941, 0.017522, 0.013924, 0.010467, 0.007711, 0.005253, 0.002545, 0.000453, 0.000004, 0.000351, 0.000301, 0.000007, 0, 0. Actual values (that is, ordinate values) on the Y-axis corresponding to line type 4 (actual transfer function in the sagittal direction) are respectively as follows: 1, 0.988892, 0.977776, 0.966632, 0.955391, 0.943999, 0.932501, 0.920949, 0.909359, 0.89774, 0.886098, 0.874441, 0.862781, 0.851126, 0.839473, 0.827823, 0.816189, 0.804579, 0.792988, 0.781421, 0.769889, 0.7584, 0.74695, 0.735542, 0.724192, 0.712904, 0.701665, 0.69047, 0.679338, 0.668337, 0.657586, 0.647066, 0.636607, 0.626152, 0.615757, 0.605446, 0.595206, 0.585021, 0.574866, 0.564755, 0.554727, 0.544852, 0.535206, 0.525717, 0.516236, 0.506742, 0.497288, 0.487889, 0.478535, 0.469196, 0.459846, 0.450529, 0.441313, 0.432249, 0.423361, 0.414568, 0.405764, 0.396927, 0.388072, 0.379277, 0.370615, 0.362081, 0.35365, 0.345304, 0.33704, 0.328896, 0.320893, 0.312944, 0.304961, 0.29692, 0.288844, 0.280846, 0.272999, 0.265232, 0.257493, 0.249839, 0.242297, 0.234805, 0.227333, 0.219948, 0.212671, 0.20542, 0.198171, 0.191011, 0.183959, 0.176913, 0.169856, 0.162897, 0.156051, 0.149196, 0.142326, 0.135575, 0.128947, 0.122296, 0.115638, 0.109149, 0.102796, 0.096362, 0.089939, 0.08387, 0.078134, 0.072435, 0.066767, 0.06132, 0.056009, 0.050597, 0.045268, 0.040416, 0.035845, 0.031107, 0.026501, 0.022598, 0.019086, 0.015367, 0.011811, 0.009039, 0.00653, 0.003578, 0.001092, 0.000225, 0.000296, 0.000237, 0.000044, 0, 0.

The abscissa in FIG. 5 represents spatial frequency in the unit of cycles per millimeter (cycles/mm). In FIG. 5, the spatial frequency ranges from 0 to 720, with intervals of 10 cycles per millimeter. Actual values (that is, ordinate values) on the Y-axis corresponding to line type 3 (actual transfer function in the tangential direction) are respectively as follows: 1, 0.695346, 0.403169, 0.150239, 0.031339, 0.026561, 0.052371, 0.07776, 0.063535, 0.044861, 0.040827, 0.042849, 0.053615, 0.068224, 0.073411, 0.068164, 0.058676, 0.051014, 0.039108, 0.025228, 0.015465, 0.017495, 0.027212, 0.030791, 0.025944, 0.014651, 0.008479, 0.012901, 0.020772, 0.025449, 0.027474, 0.02882, 0.028675, 0.02476, 0.017287, 0.01637, 0.017357, 0.013998, 0.017064, 0.02814, 0.026228, 0.022807, 0.02943, 0.028085, 0.026607, 0.035384, 0.042859, 0.038684, 0.027244, 0.015012, 0.011542, 0.017332, 0.02061, 0.019196, 0.017384, 0.014284, 0.011459, 0.009736, 0.008987, 0.00876, 0.008623, 0.004929, 0.002773, 0.006026, 0.003171, 0.003745, 0.001443, 0.000217, 0.00129, 0.001414, 0.000538, 0.000283, 0. Actual values (that is, ordinate values) on the Y-axis corresponding to line type 4 (actual transfer function in the sagittal direction) are respectively as follows: 1, 0.663046, 0.215287, 0.079246, 0.15338, 0.129933, 0.045434, 0.04103, 0.066431, 0.029356, 0.022086, 0.005608, 0.015339, 0.03849, 0.024411, 0.00677, 0.00615, 0.02143, 0.032545, 0.031277, 0.024655, 0.018109, 0.011251, 0.004874, 0.001822, 0.002934, 0.004052, 0.004855, 0.00334, 0.00194, 0.004404, 0.009478, 0.015964, 0.021848, 0.022122, 0.015966, 0.00744, 0.003243, 0.007145, 0.014012, 0.013923, 0.007531, 0.006731, 0.013466, 0.014058, 0.008703, 0.010625, 0.018174, 0.018288, 0.016482, 0.02614, 0.043361, 0.051317, 0.046177, 0.035356, 0.024427, 0.017856, 0.013577, 0.011505, 0.010552, 0.009352, 0.007872, 0.004684, 0.000505, 0.000346, 0.000051, 0, 0.000012, 0, 0.000001, 0, 0, 0.

The abscissa in FIG. 6 represents spatial frequency in the unit of cycles per millimeter (cycles/mm). In FIG. 6, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.98621, 0.971682, 0.955875, 0.93896, 0.92124, 0.902913, 0.88416, 0.865186, 0.84618, 0.827276, 0.808594, 0.790239, 0.772293, 0.7548, 0.737794, 0.721296, 0.705319, 0.689857, 0.6749, 0.660429, 0.646424, 0.632859, 0.619711, 0.606955, 0.594625, 0.582828, 0.571532, 0.560531, 0.549732, 0.539181, 0.528893, 0.518838, 0.508985, 0.499311, 0.489884, 0.480841, 0.472131, 0.46355, 0.455037, 0.446643, 0.43837, 0.430182, 0.422031, 0.413874, 0.405774, 0.397835, 0.389966, 0.381978, 0.373792, 0.365397, 0.356865, 0.348275, 0.339541, 0.330533, 0.321323, 0.312024, 0.30255, 0.292774, 0.282696, 0.272368, 0.261904, 0.251406, 0.240853, 0.23023, 0.21967, 0.209292, 0.199041, 0.188882, 0.178943, 0.169342, 0.16006, 0.151072, 0.142393, 0.134057, 0.126127, 0.118613, 0.111402, 0.104444, 0.097851, 0.091673, 0.085808, 0.08016, 0.074665, 0.0693, 0.064105, 0.059105, 0.054291, 0.049574, 0.044771, 0.039871, 0.035087, 0.030515, 0.026111, 0.021811, 0.01755, 0.013516, 0.010095, 0.007071, 0.003781, 0.000809, 0, 0, 0.000191, 0.000075, 0, 0, 0.000008, 0.000002, 0, 0, 0.000001, 0, 0, 0, 0, 0, 0, 0, 0, 0, 0, 0, 0, 0, 0. Actual values (that is, ordinate values) on the Y-axis corresponding to line type 4 (actual transfer function in the sagittal direction) are respectively as follows: 1, 0.988353, 0.976309, 0.96356, 0.950121, 0.936076, 0.921486, 0.906415, 0.890943, 0.875159, 0.859162, 0.843047, 0.826905, 0.810821, 0.794879, 0.779153, 0.7637, 0.748568, 0.7338, 0.719428, 0.705465, 0.691919, 0.67879, 0.66608, 0.653789, 0.641886, 0.630291, 0.619032, 0.608264, 0.597997, 0.588057, 0.578338, 0.568816, 0.559476, 0.550311, 0.541296, 0.532393, 0.523576, 0.514837, 0.506248, 0.497927, 0.489804, 0.481689, 0.473537, 0.465393, 0.45727, 0.449155, 0.441005, 0.432772, 0.424516, 0.416339, 0.408252, 0.40022, 0.392173, 0.384032, 0.375751, 0.367321, 0.358875, 0.350547, 0.342246, 0.333844, 0.325391, 0.316955, 0.308471, 0.29988, 0.291275, 0.282734, 0.274168, 0.265524, 0.256985, 0.248678, 0.240455, 0.232197, 0.224008, 0.215972, 0.208046, 0.200219, 0.192585, 0.185193, 0.177973, 0.170887, 0.163975, 0.157265, 0.150742, 0.144377, 0.138127, 0.131989, 0.126022, 0.120201, 0.114394, 0.108593, 0.102951, 0.097421, 0.091746, 0.085993, 0.080554, 0.07541, 0.070159, 0.064762, 0.059487, 0.054303, 0.048959, 0.043592, 0.03859, 0.033872, 0.029085, 0.024405, 0.020284, 0.016623, 0.013058, 0.009615, 0.00651, 0.003825, 0.001614, 0.000224, 0, 0.000262, 0.000241, 0.000016, 0, 0, 0.000014, 0, 0, 0.

Figure 7:
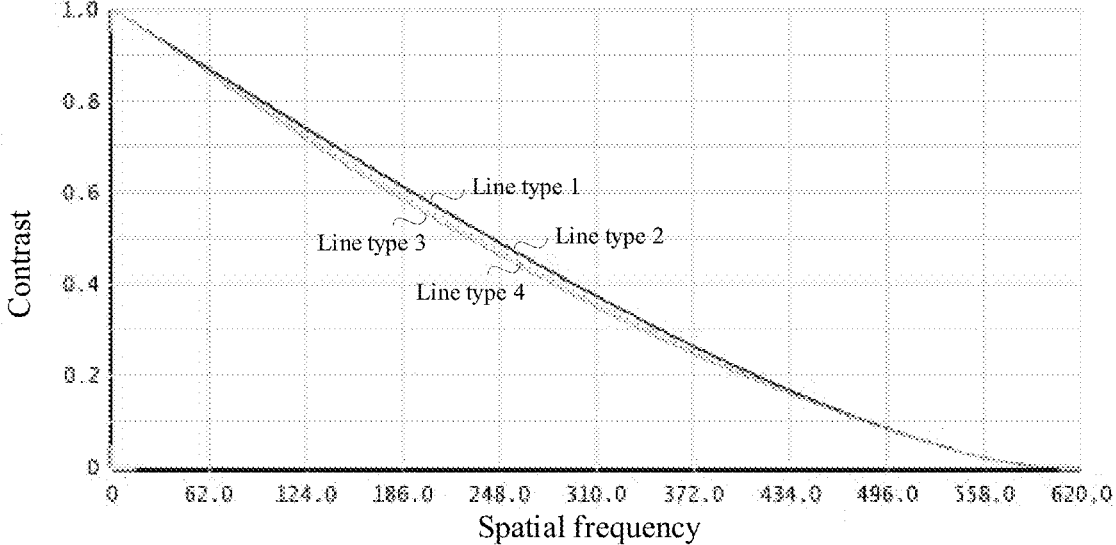
FIG. 7 is an MTF graph of a biological body imaging system at a field of view of 0.707 in a first lens combination manner according to Embodiment 1.
Figure 8:
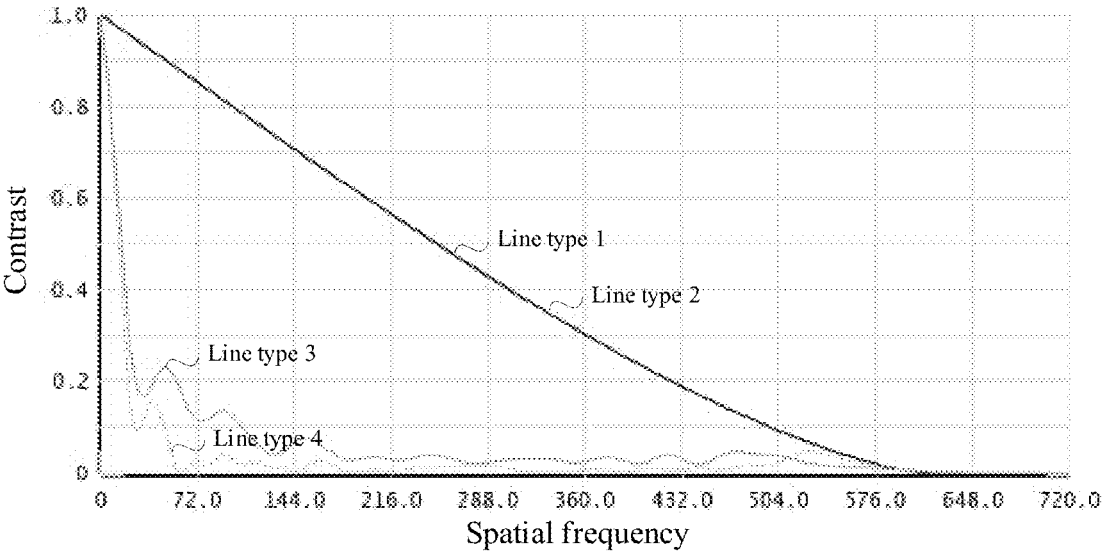
FIG. 8 is an MTF graph of a biological body imaging system at a field of view of 0.707 in a second lens combination manner according to Embodiment 1.
Figure 9:
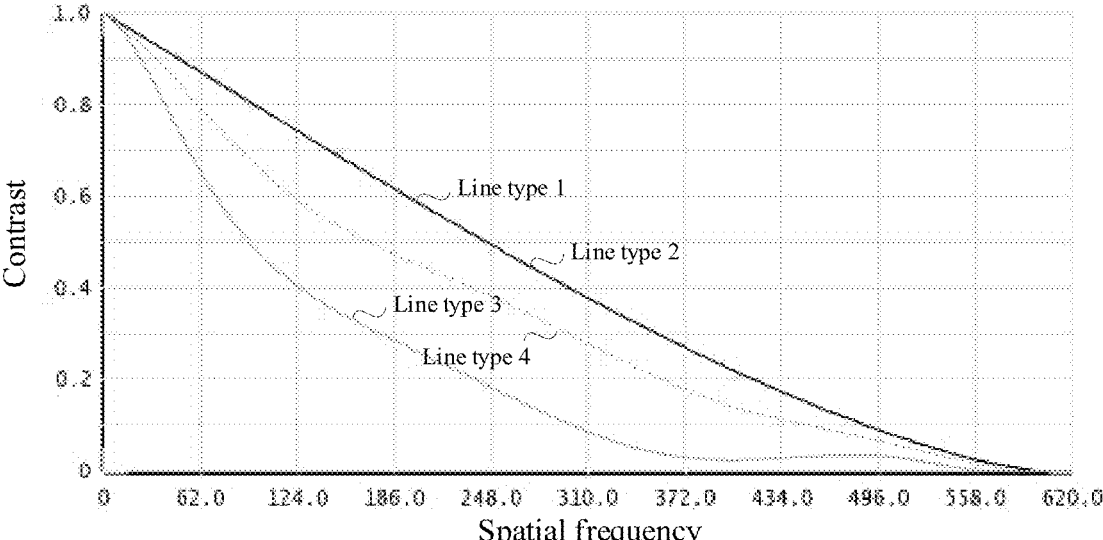
FIG. 9 is an MTF graph of a biological body imaging system at a field of view of 0.707 in a third lens combination manner according to Embodiment 1.

Referring to FIGS. 7 to 9, FIG. 7 is an MTF graph of a biological body imaging system 10 at a field of view of 0.707 according to Embodiment 1, FIG. 8 is an MTF graph of a biological body imaging system 10a at a field of view of 0.707 according to Embodiment 1, and FIG. 9 is an MTF graph of a biological body imaging system 10b at a field of view of 0.707 according to Embodiment 1.

The abscissa in FIG. 7 represents spatial frequency in the unit of cycles per millimeter (cycles/mm). In FIG. 7, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989015, 0.978098, 0.967277, 0.956424, 0.945424, 0.934297, 0.923081, 0.911776, 0.900377, 0.888896, 0.877344, 0.865731, 0.854066, 0.842361, 0.830629, 0.818881, 0.80713, 0.795387, 0.783664, 0.771972, 0.760321, 0.748716, 0.737167, 0.725687, 0.714278, 0.702931, 0.691646, 0.680437, 0.669372, 0.658568, 0.648003, 0.637504, 0.627013, 0.616586, 0.606244, 0.595972, 0.585747, 0.575546, 0.565382, 0.555294, 0.545349, 0.535616, 0.526023, 0.51642, 0.506787, 0.497179, 0.487608, 0.478064, 0.468516, 0.45894, 0.449381, 0.439914, 0.430587, 0.421417, 0.412327, 0.403218, 0.394067, 0.384893, 0.375777, 0.366803, 0.35796, 0.349213, 0.340559, 0.332008, 0.323591, 0.315322, 0.307123, 0.298915, 0.290673, 0.282421, 0.27428, 0.266331, 0.258489, 0.250699, 0.243031, 0.235523, 0.228095, 0.220712, 0.213455, 0.206351, 0.199302, 0.192273, 0.185369, 0.178609, 0.171874, 0.165136, 0.15852, 0.152038, 0.14555, 0.13904, 0.132657, 0.126401, 0.120105, 0.113779, 0.107612, 0.101567, 0.095406, 0.089223, 0.08338, 0.077847, 0.072297, 0.066729, 0.061362, 0.056111, 0.050721, 0.045387, 0.040522, 0.035928, 0.031142, 0.026477, 0.022532, 0.018989, 0.015224, 0.011625, 0.008835, 0.006328, 0.003389, 0.000947, 0.00017, 0.000314, 0.000246, 0.000014, 0, 0. Actual values (that is, ordinate values) on the Y-axis corresponding to line type 4 (actual transfer function in the sagittal direction) are respectively as follows: 1, 0.989055, 0.978203, 0.967487, 0.956783, 0.94597, 0.935068, 0.924118, 0.913114, 0.90205, 0.890932, 0.879768, 0.868562, 0.857319, 0.846047, 0.834752, 0.823443, 0.812128, 0.800814, 0.789508, 0.778221, 0.766957, 0.755722, 0.744522, 0.733366, 0.722259, 0.711192, 0.700164, 0.68918, 0.678309, 0.667677, 0.657267, 0.646901, 0.636521, 0.626185, 0.615915, 0.605695, 0.595507, 0.585333, 0.575183, 0.565086, 0.555115, 0.545355, 0.535737, 0.526103, 0.516434, 0.506785, 0.497172, 0.487581, 0.477989, 0.468372, 0.458768, 0.449241, 0.439848, 0.430628, 0.421495, 0.412337, 0.403138, 0.393921, 0.384752, 0.375702, 0.366779, 0.357972, 0.349252, 0.340603, 0.332081, 0.32372, 0.315428, 0.307109, 0.298748, 0.290373, 0.282086, 0.273958, 0.265936, 0.257981, 0.250127, 0.242395, 0.234743, 0.227156, 0.219673, 0.212307, 0.205003, 0.197743, 0.190586, 0.183545, 0.176543, 0.169565, 0.162692, 0.155932, 0.149188, 0.142453, 0.135832, 0.129324, 0.122807, 0.116293, 0.109928, 0.103678, 0.09735, 0.091027, 0.085015, 0.079301, 0.07363, 0.067992, 0.062542, 0.057196, 0.051746, 0.04637, 0.041437, 0.036768, 0.031952, 0.027269, 0.023257, 0.019631, 0.01584, 0.012236, 0.009398, 0.006825, 0.003843, 0.001308, 0.000313, 0.00027, 0.000219, 0.000081, 0.000012, 0.

The abscissa in FIG. 8 represents spatial frequency in the unit of cycles per millimeter (cycles/mm). In FIG. 8, the spatial frequency ranges from 0 to 720, with intervals of 10 cycles per millimeter. Actual values (that is, ordinate values) on the Y-axis corresponding to line type 3 (actual transfer function in the tangential direction) are respectively as follows: 1, 0.700743, 0.329649, 0.167578, 0.204311, 228271, 0.173682, 0.116644, 0.118336, 0.136436, 0.119212, 0.082198, 0.050298, 0.040437, 0.057033, 0.07589, 0.068379, 0.04777, 0.030888, 0.028779, 0.033711, 0.032481, 0.027403, 0.030176, 0.038317, 0.038073, 0.031132, 0.023261, 0.02077, 0.023986, 0.028269, 0.031041, 0.032293, 0.031497, 0.02805, 0.02274, 0.024358, 0.031815, 0.033703, 0.026068, 0.019344, 0.028684, 0.039418, 0.033498, 0.020462, 0.022213, 0.037697, 0.0466, 0.044244, 0.040601, 0.03944, 0.034749, 0.026503, 0.019684, 0.016045, 0.013903, 0.012497, 0.01201, 0.010668, 0.0091, 0.006227, 0.003104, 0.002291, 0.002484, 0.001191, 0.000445, 0.000269, 0.000076, 0, 0.000006, 0, 0, 0. Actual values (that is, ordinate values) on the Y-axis corresponding to line type 4 (actual transfer function in the sagittal direction) are respectively as follows: 1, 0.649618, 0.204956, 0.104558, 0.152042, 0.06732, 0, 0.024391, 0.018408, 0.040555, 0.026629, 0.022859, 0.020019, 0.01214, 0.00886, 0.005481, 0.02643, 0.021937, 0.005911, 0.003034, 0.007057, 0.003663, 0.002057, 0.010701, 0.01199, 0.01213, 0.012977, 0.014483, 0.015589, 0.015237, 0.012923, 0.007967, 0.002465, 0.002409, 0.001303, 0.002875, 0.00796, 0.009056, 0.00417, 0.001759, 0.006524, 0.011076, 0.007443, 0.005671, 0.011002, 0.012048, 0.007694, 0.011205, 0.018034, 0.017311, 0.019334, 0.030641, 0.0434, 0.047197, 0.04176, 0.033458, 0.025505, 0.02017, 0.016013, 0.012448, 0.00917, 0.004588, 0.000685, 0.000282, 0, 0, 0.000005, 0, 0.000001, 0, 0, 0, 0.

The abscissa in FIG. 9 represents spatial frequency in the unit of cycles per millimeter (cycles/mm). In FIG. 9, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.985227, 0.967729, 0.94554, 0.919441, 0.890654, 0.859789, 0.827384, 0.794145, 0.760753, 0.727736, 0.695549, 0.664533, 0.634964, 0.607008, 0.580772, 0.556269, 0.533478, 0.512335, 0.492752, 0.474605, 0.45777, 0.442126, 0.427553, 0.413937, 0.40115, 0.389055, 0.377609, 0.366892, 0.356837, 0.347206, 0.33786, 0.328781, 0.319942, 0.311301, 0.302802, 0.294377, 0.286018, 0.277764, 0.269635, 0.261636, 0.25369, 0.245676, 0.237571, 0.22941, 0.221201, 0.212931, 0.204574, 0.196114, 0.187638, 0.179264, 0.170969, 0.16267, 0.154362, 0.146069, 0.137811, 0.12962, 0.1216, 0.11385, 0.106321, 0.09895, 0.09184, 0.085098, 0.07867, 0.072481, 0.066555, 0.060939, 0.055694, 0.050864, 0.046432, 0.042385, 0.038751, 0.035541, 0.032706, 0.030224, 0.028159, 0.026533, 0.025238, 0.024231, 0.023622, 0.023431, 0.023478, 0.023685, 0.024184, 0.024983, 0.025871, 0.026762, 0.027777, 0.028921, 0.030023, 0.031, 0.03189, 0.032697, 0.033386, 0.033938, 0.034355, 0.03458, 0.034499, 0.033987, 0.032929, 0.031446, 0.029821, 0.027929, 0.025401, 0.02249, 0.019803, 0.017172, 0.014037, 0.010729, 0.007976, 0.005505, 0.002698, 0.000348, 0, 0.000024, 0.000158, 0.000016, 0, 0, 0.00001, 0.000001, 0, 0, 0.000001, 0. Actual values (that is, ordinate values) on the Y-axis corresponding to line type 4 (actual transfer function in the sagittal direction) are respectively as follows: 1, 0.988297, 0.975866, 0.962146, 0.947196, 0.931196, 0.914259, 0.8965, 0.878065, 0.859114, 0.83982, 0.820351, 0.800858, 0.781481, 0.762349, 0.743581, 0.725273, 0.707504, 0.690322, 0.673771, 0.65789, 0.642693, 0.628164, 0.614292, 0.601089, 0.588523, 0.576514, 0.565033, 0.55413, 0.543828, 0.534115, 0.524902, 0.516026, 0.507408, 0.499049, 0.490934, 0.483023, 0.475252, 0.467538, 0.459904, 0.452442, 0.445154, 0.437972, 0.430807, 0.423558, 0.416206, 0.408777, 0.401267, 0.393655, 0.385895, 0.377946, 0.369908, 0.361919, 0.353937, 0.345855, 0.337644, 0.329298, 0.320786, 0.312103, 0.30341, 0.294857, 0.28632, 0.277662, 0.26904, 0.260619, 0.252299, 0.243961, 0.235637, 0.227369, 0.21914, 0.210976, 0.203062, 0.195507, 0.188139, 0.180863, 0.173886, 0.167321, 0.160975, 0.154762, 0.148872, 0.143384, 0.138104, 0.132956, 0.128104, 0.123588, 0.119227, 0.114955, 0.110901, 0.107076, 0.10332, 0.099579, 0.09594, 0.092399, 0.088841, 0.085216, 0.081541, 0.077824, 0.074062, 0.070288, 0.066554, 0.062809, 0.058921, 0.054828, 0.050533, 0.046148, 0.041837, 0.037552, 0.033143, 0.028776, 0.024747, 0.02096, 0.017166, 0.013583, 0.010551, 0.007745, 0.004709, 0.002059, 0.000645, 0.00021, 0.000147, 0.000159, 0.000093, 0.000002, 0, 0.

Figure 10:
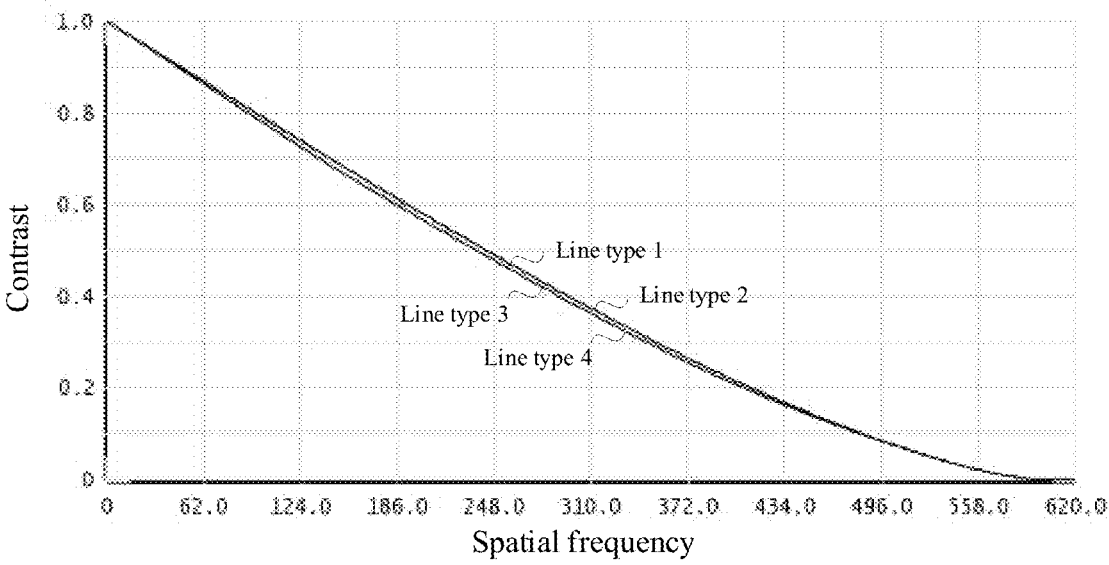
FIG. 10 is an MTF graph of a biological body imaging system at a central field of view in a first lens combination manner according to Embodiment 1.
Figure 11:
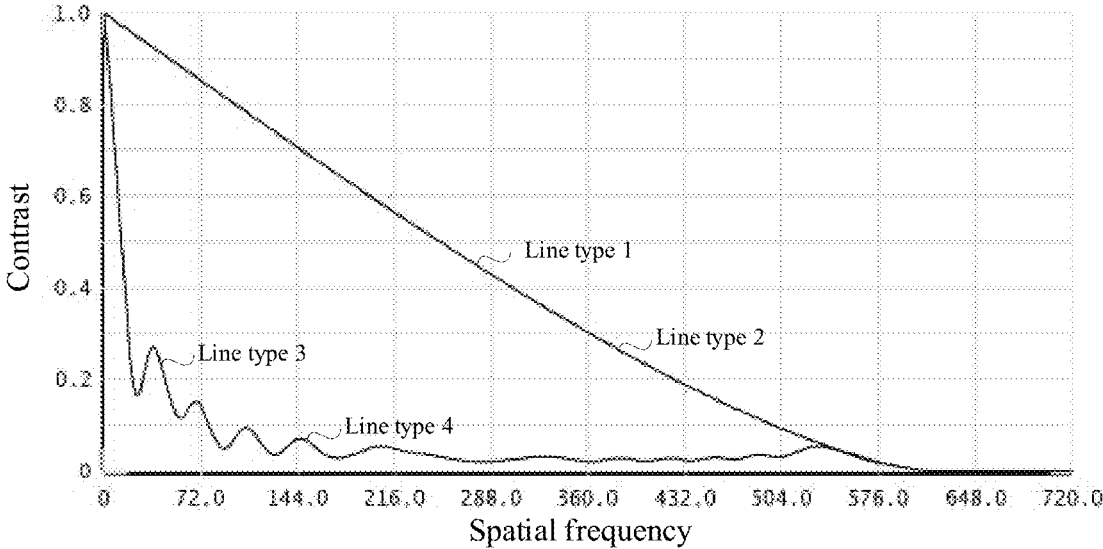
FIG. 11 is an MTF graph of a biological body imaging system at a central field of view in a second lens combination manner according to Embodiment 1.
Figure 12:
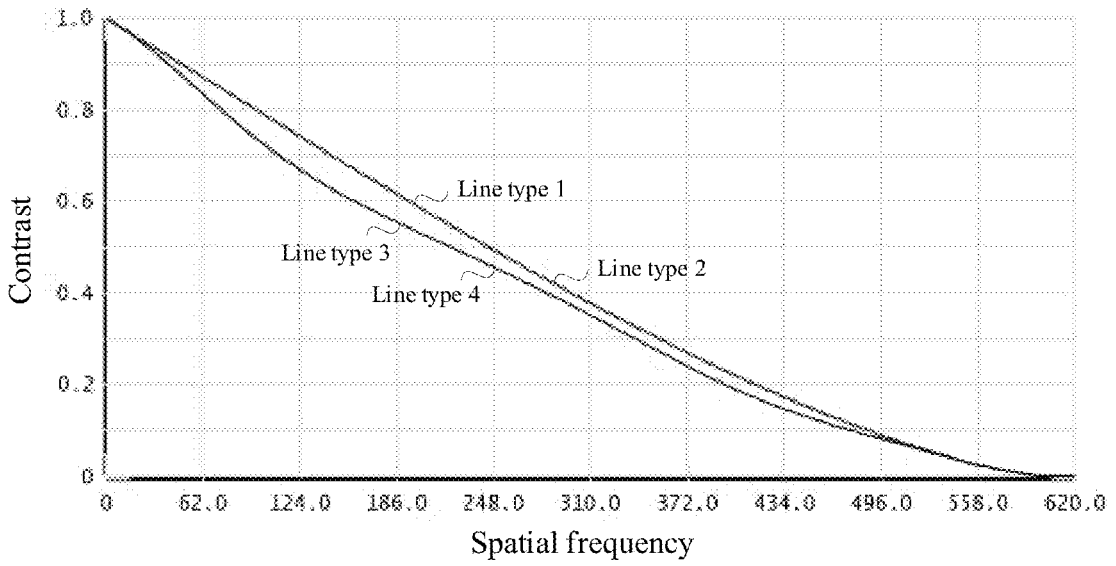
FIG. 12 is an MTF graph of a biological body imaging system at a central field of view in a third lens combination manner according to Embodiment 1.

Referring to FIGS. 10 to 12, FIG. 10 is an MTF graph of a biological body imaging system 10 at a central field according to Embodiment 1, FIG. 11 is an MTF graph of a biological body imaging system 10a at a central field of view according to Embodiment 1, and FIG. 12 is an MTF graph of a biological body imaging system 10b at a central field of view according to Embodiment 1.

The abscissa in FIG. 10 represents spatial frequency in the unit of cycles per millimeter (cycles/mm). In FIG. 10, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989061, 0.978207, 0.967478, 0.956748, 0.945899, 0.934956, 0.923957, 0.912905, 0.901796, 0.890642, 0.879456, 0.868245, 0.857018, 0.845786, 0.834559, 0.823345, 0.812153, 0.800991, 0.789866, 0.778784, 0.767751, 0.756767, 0.745838, 0.734969, 0.72416, 0.713403, 0.70269, 0.692023, 0.681463, 0.671142, 0.661037, 0.650971, 0.640879, 0.630819, 0.620809, 0.610832, 0.60087, 0.590906, 0.580945, 0.571011, 0.561178, 0.551539, 0.542024, 0.532471, 0.522859, 0.513247, 0.503648, 0.494048, 0.484425, 0.47476, 0.465085, 0.455456, 0.44594, 0.436582, 0.427297, 0.417967, 0.408576, 0.399155, 0.389762, 0.380459, 0.371271, 0.362198, 0.3532, 0.34425, 0.335415, 0.326747, 0.318146, 0.309511, 0.300834, 0.292147, 0.283545, 0.275093, 0.266761, 0.25852, 0.250387, 0.242373, 0.234463, 0.226652, 0.218957, 0.211385, 0.203905, 0.19651, 0.189235, 0.182083, 0.175007, 0.167997, 0.161106, 0.154336, 0.147619, 0.140948, 0.134397, 0.127963, 0.121549, 0.115167, 0.108928, 0.1028, 0.096616, 0.090448, 0.08456, 0.078949, 0.073404, 0.067907, 0.062568, 0.057307, 0.051946, 0.046654, 0.04176, 0.037108, 0.03233, 0.02768, 0.023647, 0.019979, 0.016188, 0.012594, 0.009717, 0.007094, 0.004106, 0.001539, 0.000411, 0.000243, 0.000196, 0.000118, 0.000052, 0. Actual values (that is, ordinate values) on the Y-axis corresponding to line type 4 (actual transfer function in the sagittal direction) are respectively as follows: 1, 0.989061, 0.978207, 0.967478, 0.956748, 0.945899, 0.934956, 0.923957, 0.912905, 0.901796, 0.890642, 0.879456, 0.868245, 0.857018, 0.845786, 0.834559, 0.823345, 0.812153, 0.800991, 0.789866, 0.778784, 0.767751, 0.756767, 0.745838, 0.734969, 0.72416, 0.713403, 0.70269, 0.692023, 0.681463, 0.671142, 0.661037, 0.650971, 0.640879, 0.630819, 0.620809, 0.610832, 0.60087, 0.590906, 0.580945, 0.571011, 0.561178, 0.551539, 0.542024, 0.532471, 0.522859, 0.513247, 0.503648, 0.494048, 0.484425, 0.47476, 0.465085, 0.455456, 0.44594, 0.436582, 0.427297, 0.417967, 0.408576, 0.399155, 0.389762, 0.380459, 0.371271, 0.362198, 0.3532, 0.34425, 0.335415, 0.326747, 0.318146, 0.309511, 0.300834, 0.292147, 0.283545, 0.275093, 0.266761, 0.25852, 0.250387, 0.242373, 0.234463, 0.226652, 0.218957, 0.211385, 0.203905, 0.19651, 0.189235, 0.182083, 0.175007, 0.167997, 0.161106, 0.154336, 0.147619, 0.140948, 0.134397, 0.127963, 0.121549, 0.115167, 0.108928, 0.1028, 0.096616, 0.090448, 0.08456, 0.078949, 0.073404, 0.067907, 0.062568, 0.057307, 0.051946, 0.046654, 0.04176, 0.037108, 0.03233, 0.02768, 0.023647, 0.019979, 0.016188, 0.012594, 0.009717, 0.007094, 0.004106, 0.001539, 0.000411, 0.000243, 0.000196, 0.000118, 0.000052, 0.

The abscissa in FIG. 11 represents spatial frequency in the unit of cycles per millimeter (cycles/mm). In FIG. 11, the spatial frequency ranges from 0 to 720, with intervals of 10 cycles per millimeter. Actual values (that is, ordinate values) on the Y-axis corresponding to line type 3 (actual transfer function in the tangential direction) are respectively as follows: 1, 0.629617, 0.230011, 0.212727, 0.256609, 0.15012, 0.121598, 0.149845, 0.08507, 0.048481, 0.083587, 0.087351, 0.047938, 0.037427, 0.063163, 0.067968, 0.044437, 0.029514, 0.030591, 0.041118, 0.051982, 0.053531, 0.046085, 0.039347, 0.035719, 0.031317, 0.025919, 0.021683, 0.020239, 0.021447, 0.024112, 0.027535, 0.031032, 0.031932, 0.029325, 0.024335, 0.020819, 0.023061, 0.027928, 0.027112, 0.022159, 0.023776, 0.02831, 0.024845, 0.023487, 0.028327, 0.028419, 0.025952, 0.03256, 0.03438, 0.030889, 0.035301, 0.046915, 0.053781, 0.050167, 0.040676, 0.031129, 0.02251, 0.016112, 0.010588, 0.005013, 0.001155, 0.000069, 0.000096, 0, 0, 0.000002, 0, 0, 0, 0, 0, 0. Actual values (that is, ordinate values) on the Y-axis corresponding to line type 4 (actual transfer function in the sagittal direction) are respectively as follows: 1, 0.629617, 0.230011, 0.212727, 0.256609, 0.15012, 0.121598, 0.149845, 0.08507, 0.048481, 0.083587, 0.087351, 0.047938, 0.037427, 0.063163, 0.067968, 0.044437, 0.029514, 0.030591, 0.041118, 0.051982, 0.053531, 0.046085, 0.039347, 0.035719, 0.031317, 0.025919, 0.021683, 0.020239, 0.021447, 0.024112, 0.027535, 0.031032, 0.031932, 0.029325, 0.024335, 0.020819, 0.023061, 0.027928, 0.027112, 0.022159, 0.023776, 0.02831, 0.024845, 0.023487, 0.028327, 0.028419, 0.025952, 0.03256, 0.03438, 0.030889, 0.035301, 0.046915, 0.053781, 0.050167, 0.040676, 0.031129, 0.02251, 0.016112, 0.010588, 0.005013, 0.001155, 0.000069, 0.000096, 0, 0, 0.000002, 0, 0, 0, 0, 0.

The abscissa in FIG. 12 represents spatial frequency in the unit of cycles per millimeter (cycles/mm). In FIG. 12, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988792, 0.977352, 0.965478, 0.953084, 0.940138, 0.9267, 0.912844, 0.898628, 0.884114, 0.869389, 0.854542, 0.839647, 0.824779, 0.810012, 0.795415, 0.781047, 0.766955, 0.753174, 0.739735, 0.726666, 0.713983, 0.70168, 0.689753, 0.678211, 0.667044, 0.656226, 0.645724, 0.635504, 0.625607, 0.616155, 0.607118, 0.598307, 0.58963, 0.581098, 0.572707, 0.564437, 0.556258, 0.548139, 0.540051, 0.531973, 0.523978, 0.516187, 0.508532, 0.500833, 0.493048, 0.485214, 0.477334, 0.469394, 0.461377, 0.45327, 0.445056, 0.436736, 0.428414, 0.420197, 0.411981, 0.403605, 0.395066, 0.386409, 0.377626, 0.368717, 0.359802, 0.350977, 0.342109, 0.33308, 0.324048, 0.315158, 0.306275, 0.297259, 0.288155, 0.279026, 0.269879, 0.26075, 0.251777, 0.24303, 0.234376, 0.225757, 0.217355, 0.209256, 0.201306, 0.193449, 0.185863, 0.178613, 0.171533, 0.164575, 0.157906, 0.15156, 0.145365, 0.139281, 0.133458, 0.127903, 0.122442, 0.117045, 0.111842, 0.106823, 0.101824, 0.096822, 0.091925, 0.087109, 0.08224, 0.077398, 0.072804, 0.068372, 0.063804, 0.059092, 0.054407, 0.049749, 0.045026, 0.040338, 0.035861, 0.031529, 0.027189, 0.023022, 0.019306, 0.015897, 0.012523, 0.009323, 0.00654, 0.004051, 0.001739, 0.000198, 0, 0.000342, 0.00033, 0. Actual values (that is, ordinate values) on the Y-axis corresponding to line type 4 (actual transfer function in the sagittal direction) are respectively as follows: 1, 0.988792, 0.977352, 0.965478, 0.953084, 0.940138, 0.9267, 0.912844, 0.898628, 0.884114, 0.869389, 0.854542, 0.839647, 0.824779, 0.810012, 0.795415, 0.781047, 0.766955, 0.753174, 0.739735, 0.726666, 0.713983, 0.70168, 0.689753, 0.678211, 0.667044, 0.656226, 0.645724, 0.635504, 0.625607, 0.616155, 0.607118, 0.598307, 0.58963, 0.581098, 0.572707, 0.564437, 0.556258, 0.548139, 0.540051, 0.531973, 0.523978, 0.516187, 0.508532, 0.500833, 0.493048, 0.485214, 0.477334, 0.469394, 0.461377, 0.45327, 0.445056, 0.436736, 0.428414, 0.420197, 0.411981, 0.403605, 0.395066, 0.386409, 0.377626, 0.368717, 0.359802, 0.350977, 0.342109, 0.33308, 0.324048, 0.315158, 0.306275, 0.297259, 0.288155, 0.279026, 0.269879, 0.26075, 0.251777, 0.24303, 0.234376, 0.225757, 0.217355, 0.209256, 0.201306, 0.193449, 0.185863, 0.178613, 0.171533, 0.164575, 0.157906, 0.15156, 0.145365, 0.139281, 0.133458, 0.127903, 0.122442, 0.117045, 0.111842, 0.106823, 0.101824, 0.096822, 0.091925, 0.087109, 0.08224, 0.077398, 0.072804, 0.068372, 0.063804, 0.059092, 0.054407, 0.049749, 0.045026, 0.040338, 0.035861, 0.031529, 0.027189, 0.023022, 0.019306, 0.015897, 0.012523, 0.009323, 0.00654, 0.004051, 0.001739, 0.000198, 0, 0.000342, 0.00033, 0.

It should be noted that in FIGS. 4 to 12, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction.

It can be known from FIGS. 4 to 12 that in the ideal state, optimal imaging effect with low distortion can be achieved when the transfer function in the tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. The MTF graph is typical at the central field of view in FIGS. 10 to 12. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

The biological body imaging system 10 in Embodiment 2 has a numerical aperture (NA) of 0.5, a field of view of 0.5 mm in the object space, telecentricity smaller than 0.2° in the image space, and an operating distance of 1.989.

TABLE 3

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 1.994 | 1.333044 | 55.794 |
| 2 | ∞ | 2.5 | 1.816000 | 46.621 |
| 3 | −3.774 | 0.12 | 1.0 | |
| 4 | 12.587 | 1.581 | 1.595220 | 67.736 |
| 5 | −7.354 | 0.118 | 1.0 | |
| 6 | 5.98 | 0.946 | 1.854779 | 24.799 |
| 7 | 2.31 | 1.619 | 1.497003 | 81.138 |
| 8 | −14.931 | 0.139 | 1.0 | |
| 9 | 2.042 | 2.509 | 1.618000 | 63.334 |
| 10 | 1.796 | 1.111 | 1.0 | |
| 11 | −0.919 | 1.161 | 1.89286 | 20.362 |
| 12 | −1.933 | 1.61 | 1.0 | |
| 13 | 3.397 | 1.598 | 2.003300 | 28.273 |
| 14 | 8.436 | 1 | | |

Table 4 shows calculated values of each optical element in Embodiment 2.

TABLE 4

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $r_4/(H + H_1)$ |
|---|---|---|---|---|---|---|---|---|---|
| 0.173 | 11.03 | 4.15 | 2.14 | -0.88 | -0.82 | 0.25 | -0.57 | 0.14 | 5.95 |

Figure 13:
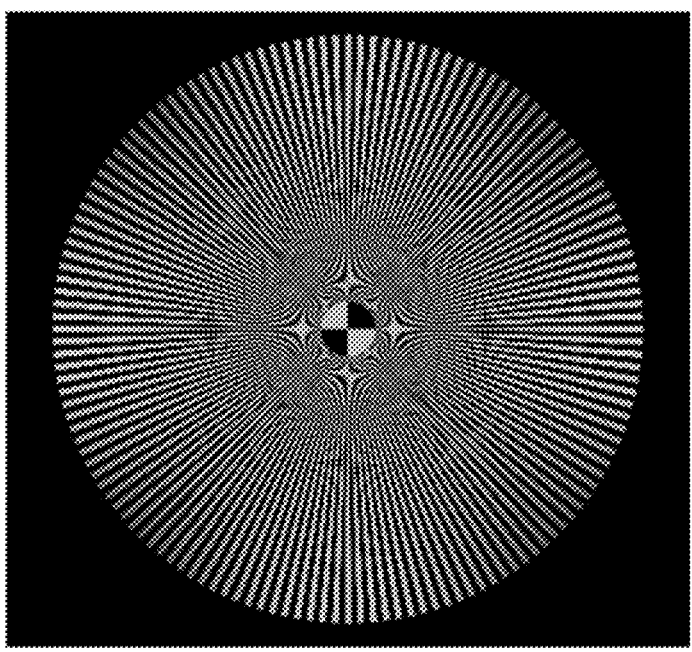
FIG. 13 is a Siemens star chart of a biological body imaging system in a first lens combination manner according to Embodiment 1.
Figure 14:
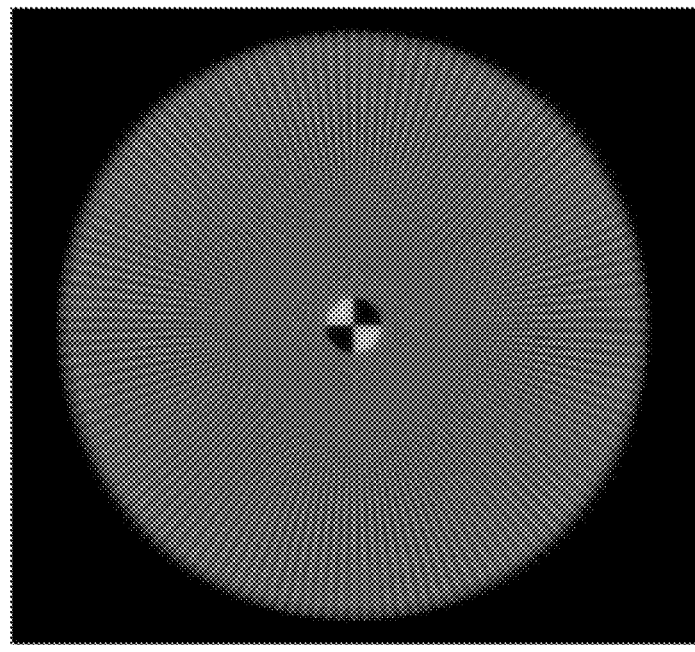
FIG. 14 is a Siemens star chart of a biological body imaging system in a second lens combination manner according to Embodiment 1.
Figure 15:
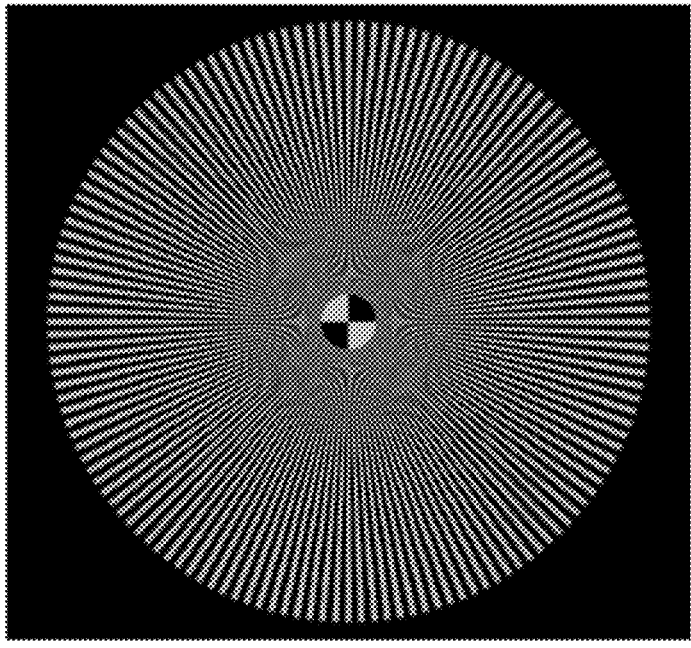
FIG. 15 is a Siemens star chart of a biological body imaging system in a third lens combination manner according to Embodiment 1.

Referring to FIGS. 13 to 15, FIG. 13 is a Siemens star chart of a biological body imaging system according to Embodiment 1; FIG. 14 is a Siemens star chart of a biological body imaging system 10a according to Embodiment 1; and FIG. 15 is a Siemens star chart of a biological body imaging system 10b according to Embodiment 1. It can be known from FIGS. 13 to 15, compared with the Siemens star chart corresponding to the biological body imaging system 10a and the Siemens star chart corresponding to the biological body imaging system 10b, the Siemens star chart corresponding to the biological body imaging system 10 is clearest. Better resolution and higher contrast indicate clearer imaging.

Unless specifically stated, the method, and symbols, meanings, and recording methods of various data of the biological body imaging system 10, the biological body imaging system 10a, and the biological body imaging system 10b in Embodiment 1 are equally applicable to the biological body imaging systems 10a and 10b in the following embodiments. Therefore, repetitive descriptions are omitted below.

Embodiment 2

The structure of the optical element of a biological body imaging system 10 in Embodiment 2 is shown in FIG. 1, and this structure is the same as that of the biological body imaging system in Embodiment 1. For the method shown in the figure, reference is made to the foregoing description, and repeated description is omitted herein. The basic parameter table of the optical elements included by the biological body imaging system 10 in Embodiment 2 shown in Table 3 includes serial number (i), curvature radius ($r_i$), central thickness ($D_i$), refractive index ($Nd_i$), and Abbe number ($vd_j$).

Figure 16:
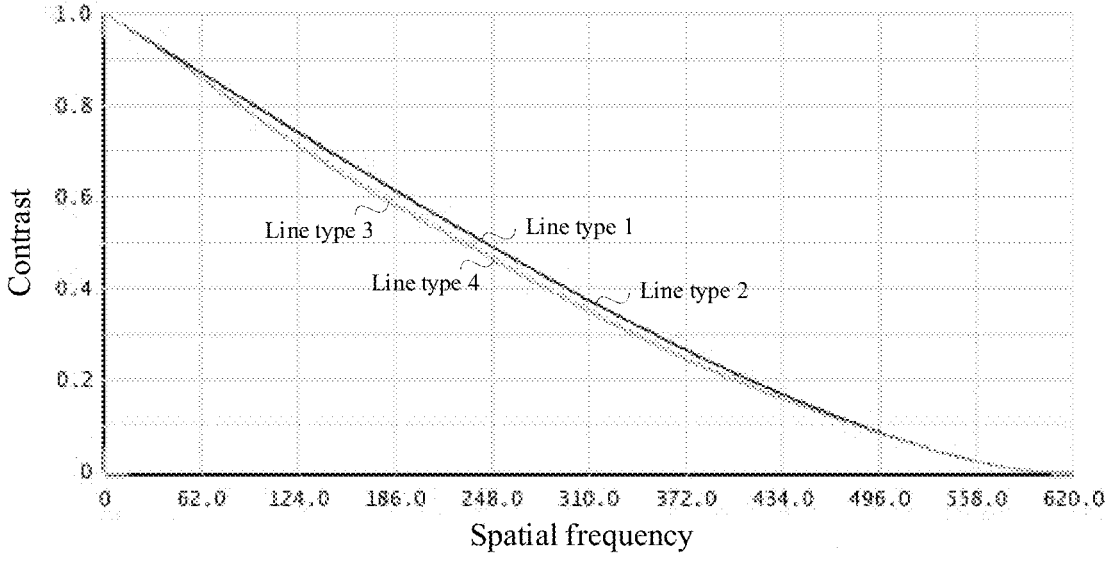
FIG. 16 is an MTF graph of a biological body imaging system at a field of view of 0.707 in a first lens combination manner according to Embodiment 2.
Figure 17:
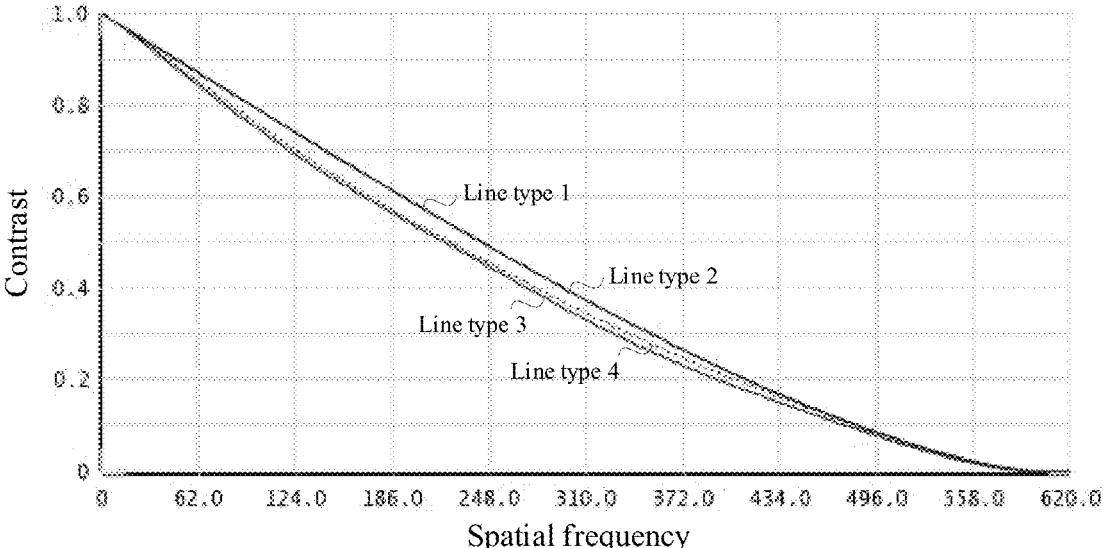
FIG. 17 is an MTF graph of a biological body imaging system at a field of view of 1.0 in a first lens combination manner according to Embodiment 2.
Figure 18:
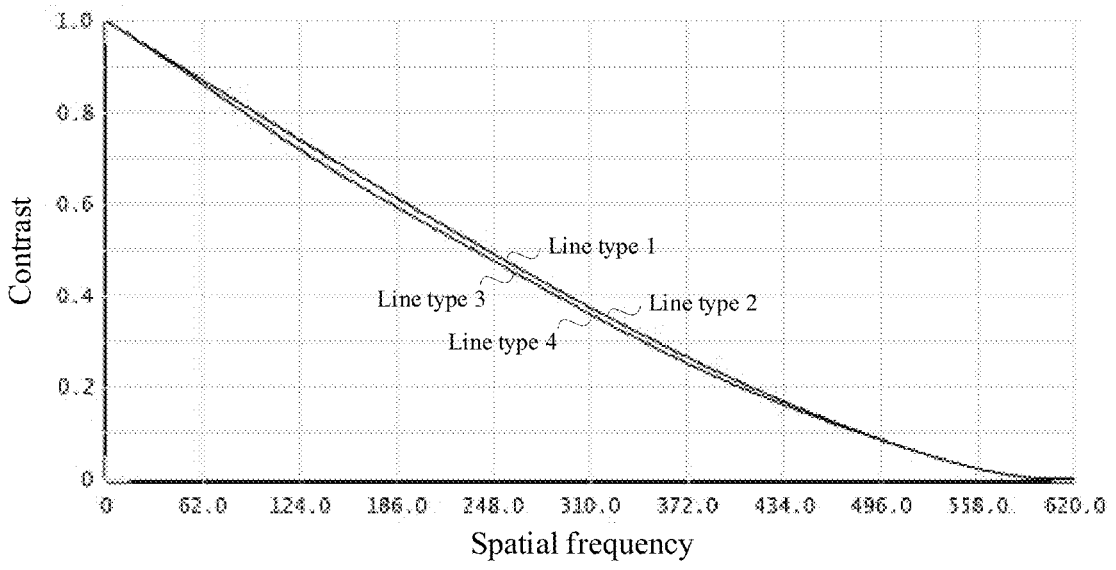
FIG. 18 is an MTF graph of a biological body imaging system at a central field of view in a first lens combination manner according to Embodiment 2.
Figure 19:
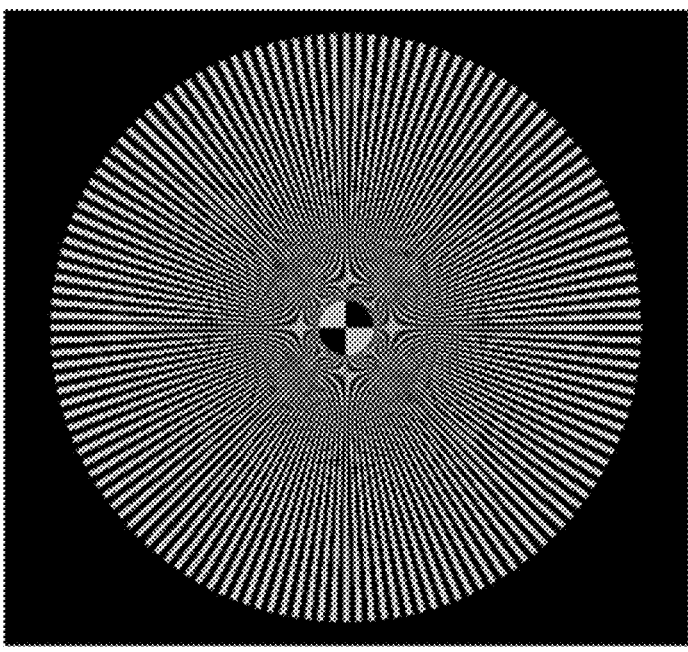
FIG. 19 is a Siemens star chart of a biological body imaging system in a first lens combination manner according to Embodiment 2.

Referring to FIGS. 16 to 18, FIGS. 16 to 18 are respective MTF graphs of a biological body imaging system 10 (that is, which is formed by a first lens set 11, a second lens set 12, a third lens set 13, and a fourth lens set 14) in a first lens combination manner at a field of view of 0.707, a field of view of 1.0, and a central field of view. Referring to FIG. 19, FIG. 19 is a Siemens star chart of a biological body imaging system 10 (that is, which is formed by a first lens set 11, a second lens set 12, a third lens set 13, and a fourth lens set 14) in a first lens combination manner according to Embodiment 2.

The abscissa in FIG. 16 represents spatial frequency in the unit of cycles per millimeter (cycles/mm). In FIG. 16, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988939, 0.977875, 0.966782, 0.955542, 0.944059, 0.932363, 0.920499, 0.908478, 0.896309, 0.884016, 0.871623, 0.859148, 0.846613, 0.834041, 0.821455, 0.808877, 0.796328, 0.78383, 0.771402, 0.759065, 0.746835, 0.734722, 0.722741, 0.710908, 0.699228, 0.687692, 0.676296, 0.665056, 0.654033, 0.643341, 0.632952, 0.622689, 0.612485, 0.602388, 0.592413, 0.582536, 0.572729, 0.562959, 0.55323, 0.543577, 0.534058, 0.524736, 0.515537, 0.506303, 0.497011, 0.487711, 0.478415, 0.469107, 0.45976, 0.450345, 0.440908, 0.431524, 0.422243, 0.413085, 0.403976, 0.394819, 0.385596, 0.376328, 0.367101, 0.358001, 0.349023, 0.340142, 0.331355, 0.322675, 0.314142, 0.305774, 0.297498, 0.289237, 0.280972, 0.272728, 0.26463, 0.256758, 0.249032, 0.241399, 0.233928, 0.226652, 0.219496, 0.212423, 0.205509, 0.198775, 0.192125, 0.185522, 0.17906, 0.172753, 0.166481, 0.160213, 0.154062, 0.148036, 0.141993, 0.135916, 0.129941, 0.124066, 0.118124, 0.112126, 0.106253, 0.100467, 0.094534, 0.088547, 0.082865, 0.077462, 0.072019, 0.06654, 0.061241, 0.056041, 0.05069, 0.045386, 0.040541, 0.035959, 0.031183, 0.026525, 0.022582, 0.019036, 0.015272, 0.011673, 0.008881, 0.00637, 0.003427, 0.000975, 0.00018, 0.000311, 0.000245, 0.00002, 0, 0. Actual values (that is, ordinate values) on the Y-axis corresponding to line type 4 (actual transfer function in the sagittal direction) are respectively as follows: 1, 0.989007, 0.978053, 0.967146, 0.956168, 0.945015, 0.933717, 0.922315, 0.910813, 0.899211, 0.887519, 0.875753, 0.863924, 0.852043, 0.840126, 0.828188, 0.816245, 0.804313, 0.792409, 0.780547, 0.768743, 0.757012, 0.745361, 0.733801, 0.722346, 0.711, 0.699758, 0.688615, 0.677573, 0.666697, 0.656114, 0.645803, 0.635582, 0.625387, 0.615267, 0.605239, 0.595282, 0.585374, 0.575492, 0.565637, 0.55583, 0.54614, 0.536657, 0.527309, 0.517931, 0.5085, 0.499071, 0.489657, 0.480243, 0.470808, 0.46133, 0.451842, 0.4424, 0.433072, 0.423906, 0.414817, 0.405687, 0.396504, 0.387299, 0.378131, 0.369063, 0.360122, 0.351313, 0.342595, 0.333938, 0.325416, 0.31708, 0.308831, 0.300568, 0.292282, 0.284007, 0.275833, 0.267825, 0.259953, 0.252189, 0.244544, 0.237024, 0.229615, 0.222309, 0.21512, 0.208044, 0.201054, 0.194138, 0.187323, 0.180608, 0.173945, 0.16732, 0.160781, 0.154326, 0.147887, 0.141456, 0.135104, 0.128824, 0.122526, 0.116222, 0.110023, 0.103898, 0.097689, 0.091472, 0.08551, 0.079806, 0.074162, 0.068564, 0.063121, 0.057758, 0.052306, 0.046935, 0.041971, 0.03726, 0.032442, 0.027766, 0.02371, 0.020027, 0.016233, 0.012641, 0.009761, 0.007132, 0.004144, 0.001574, 0.000427, 0.000239, 0.000192, 0.000123, 0.000058, 0.

The abscissa in FIG. 17 represents spatial frequency in the unit of cycles per millimeter (cycles/mm). In FIG. 17, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988603, 0.976989, 0.964987, 0.952579, 0.939807, 0.92678, 0.91361, 0.900372, 0.887122, 0.873901, 0.860743, 0.847683, 0.834742, 0.821919, 0.809214, 0.796645, 0.784221, 0.77193, 0.759768, 0.747748, 0.735874, 0.724134, 0.712526, 0.701067, 0.689756, 0.678561, 0.667482, 0.656555, 0.645841, 0.635412, 0.62523, 0.615143, 0.605094, 0.595128, 0.585258, 0.575469, 0.565727, 0.555991, 0.546282, 0.536664, 0.527173, 0.517821, 0.508537, 0.499209, 0.48982, 0.480407, 0.470985, 0.461549, 0.452064, 0.442499, 0.432922, 0.423439, 0.414053, 0.404731, 0.395432, 0.386119, 0.376769, 0.367384, 0.358077, 0.348957, 0.339964, 0.331022, 0.322196, 0.313562, 0.30509, 0.296733, 0.288473, 0.280296, 0.27217, 0.264105, 0.25623, 0.248619, 0.241148, 0.233741, 0.226517, 0.219533, 0.212655, 0.205817, 0.199141, 0.19267, 0.186256, 0.179843, 0.17356, 0.167435, 0.161313, 0.155153, 0.149091, 0.143144, 0.137157, 0.131107, 0.125139, 0.119263, 0.113324, 0.107327, 0.101433, 0.095627, 0.089739, 0.083849, 0.078242, 0.072877, 0.067471, 0.062035, 0.056781, 0.051674, 0.046536, 0.041491, 0.03681, 0.032368, 0.027871, 0.023533, 0.019755, 0.016333, 0.012855, 0.009508, 0.006661, 0.004187, 0.001884, 0.000257, 0, 0.000079, 0.000118, 0.000000, 0, 0. Actual values (that is, ordinate values) on the Y-axis corresponding to line type 4 (actual transfer function in the sagittal direction) are respectively as follows: 1, 0.988998, 0.977829, 0.966366, 0.954627, 0.942664, 0.930531, 0.918278, 0.905941, 0.893547, 0.881114, 0.86866, 0.856206, 0.843771, 0.831356, 0.818969, 0.806632, 0.794361, 0.782155, 0.770018, 0.757976, 0.746041, 0.734206, 0.722474, 0.710869, 0.699397, 0.688036, 0.676781, 0.66565, 0.654706, 0.644064, 0.633697, 0.623437, 0.613218, 0.603087, 0.593059, 0.583122, 0.573252, 0.563417, 0.553624, 0.543908, 0.534335, 0.524978, 0.515764, 0.50654, 0.497283, 0.488043, 0.478834, 0.469646, 0.460452, 0.451226, 0.442008, 0.432868, 0.423862, 0.415018, 0.406259, 0.397478, 0.388657, 0.379815, 0.371026, 0.362368, 0.353843, 0.345435, 0.33712, 0.328893, 0.320801, 0.312875, 0.305024, 0.297159, 0.28926, 0.281353, 0.273544, 0.265906, 0.258376, 0.25091, 0.243548, 0.236312, 0.229149, 0.222036, 0.215021, 0.208115, 0.201249, 0.194399, 0.187633, 0.180962, 0.174296, 0.167614, 0.161008, 0.154485, 0.147938, 0.141355, 0.134857, 0.128443, 0.121983, 0.115492, 0.109131, 0.102871, 0.096514, 0.090149, 0.084102, 0.078362, 0.072662, 0.066999, 0.061543, 0.056212, 0.050789, 0.045458, 0.040594, 0.036011, 0.031281, 0.026689, 0.022782, 0.019261, 0.01555, 0.012006, 0.009227, 0.006699, 0.003735, 0.001219, 0.000276, 0.00028, 0.000227, 0.000067, 0, 0.

The abscissa in FIG. 18 represents spatial frequency in the unit of cycles per millimeter (cycles/mm). In FIG. 18, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989048, 0.978154, 0.967336, 0.95647, 0.945441, 0.934274, 0.923009, 0.911646, 0.900187, 0.888646, 0.877041, 0.865384, 0.853691, 0.84198, 0.83027, 0.818577, 0.806917, 0.795307, 0.783762, 0.772296, 0.760919, 0.749638, 0.73846, 0.727395, 0.716444, 0.705601, 0.694856, 0.684203, 0.673702, 0.663485, 0.65353, 0.643652, 0.63378, 0.623966, 0.614222, 0.604527, 0.594858, 0.585196, 0.575537, 0.565895, 0.556341, 0.546975, 0.537727, 0.528426, 0.519049, 0.509652, 0.500247, 0.490817, 0.481345, 0.471813, 0.462246, 0.45269, 0.44322, 0.433901, 0.424643, 0.415317, 0.405916, 0.396477, 0.387048, 0.377679, 0.368416, 0.359283, 0.350221, 0.341184, 0.332262, 0.323527, 0.314872, 0.306183, 0.297467, 0.288761, 0.280143, 0.271671, 0.263346, 0.255156, 0.247087, 0.239132, 0.231312, 0.223639, 0.216093, 0.208663, 0.201356, 0.194178, 0.187118, 0.18017, 0.173321, 0.166569, 0.159922, 0.153371, 0.146887, 0.140466, 0.134135, 0.127882, 0.121658, 0.115469, 0.10938, 0.10336, 0.097293, 0.091239, 0.085397, 0.079783, 0.074266, 0.06882, 0.063486, 0.058196, 0.052834, 0.047545, 0.042597, 0.037871, 0.033081, 0.028434, 0.024319, 0.02055, 0.016749, 0.013169, 0.010216, 0.007502, 0.004522, 0.00193, 0.000589, 0.000201, 0.000154, 0.000171, 0.000115, 0. Actual values (that is, ordinate values) on the Y-axis corresponding to line type 4 (actual transfer function in the sagittal direction) are respectively as follows: 1, 0.989048, 0.978154, 0.967336, 0.95647, 0.945441, 0.934274, 0.923009, 0.911646, 0.900187, 0.888646, 0.877041, 0.865384, 0.853691, 0.84198, 0.83027, 0.818577, 0.806917, 0.795307, 0.783762, 0.772296, 0.760919, 0.749638, 0.73846, 0.727395, 0.716444, 0.705601, 0.694856, 0.684203, 0.673702, 0.663485, 0.65353, 0.643652, 0.63378, 0.623966, 0.614222, 0.604527, 0.594858, 0.585196, 0.575537, 0.565895, 0.556341, 0.546975, 0.537727, 0.528426, 0.519049, 0.509652, 0.500247, 0.490817, 0.481345, 0.471813, 0.462246, 0.45269, 0.44322, 0.433901, 0.424643, 0.415317, 0.405916, 0.396477, 0.387048, 0.377679, 0.368416, 0.359283, 0.350221, 0.341184, 0.332262, 0.323527, 0.314872, 0.306183, 0.297467, 0.288761, 0.280143, 0.271671, 0.263346, 0.255156, 0.247087, 0.239132, 0.231312, 0.223639, 0.216093, 0.208663, 0.201356, 0.194178, 0.187118, 0.18017, 0.173321, 0.166569, 0.159922, 0.153371, 0.146887, 0.140466, 0.134135, 0.127882, 0.121658, 0.115469, 0.10938, 0.10336, 0.097293, 0.091239, 0.085397, 0.079783, 0.074266, 0.06882, 0.063486, 0.058196, 0.052834, 0.047545, 0.042597, 0.037871, 0.033081, 0.028434, 0.024319, 0.02055, 0.016749, 0.013169, 0.010216, 0.007502, 0.004522, 0.00193, 0.000589, 0.000201, 0.000154, 0.000171, 0.000115, 0.

It should be noted that in FIGS. 16 to 18, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction. It can be known from FIGS. 16 to 18 that in the ideal state, optimal imaging effect with low distortion can be achieved when the transfer function in the

TABLE 5

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 2.15 | 1.333044 | 55.794 |
| 2 | ∞ | 1.96 | 1.816000 | 46.621 |
| 3 | −3.546 | 0.141 | 1.0 | |
| 4 | 36.342 | 1.318 | 1.595220 | 67.736 |
| 5 | −5.794 | 0.115 | 1.0 | |
| 6 | 7.487 | 0.943 | 1.854779 | 24.799 |
| 7 | 2.26 | 2.308 | 1.595220 | 67.736 |
| 8 | −13.725 | 0.12 | 1.0 | |
| 9 | 2.013 | 2.494 | 1.622800 | 56.913 |
| 10 | 1.565 | 1.087 | 1.0 | |
| 11 | −0.855 | 1.031 | 1.854779 | 24.799 |
| 12 | −1.706 | 1.409 | 1.0 | |
| 13 | 3.163 | 1.711 | 1.816000 | 46.621 |
| 14 | 13.327 | 1.22 | | |

Table 6 shows calculated values of each optical element in Embodiment 3.

TABLE 6

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $r_4/(H + H_1)$ |
|---|---|---|---|---|---|---|---|---|---|
| 0.170 | 7.2 | 2.24 | 1.99 | -0.96 | -0.82 | 0.20 | -0.54 | 0.14 | 15.86 | tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

Embodiment 3

The structure of the optical element of a biological body imaging system 10 in Embodiment 2 is shown in FIG. 1, and this structure is the same as that of the biological body imaging system in Embodiment 1. For the method shown in the figure, reference is made to the foregoing description, and repeated description is omitted herein. The basic parameter table of the optical elements included by the biological body imaging system 10 in Embodiment 3 shown in Table includes serial number (i), curvature radius ($r_i$), central thickness ($D_i$), refractive index ($Nd_i$), and Abbe number ($vd_j$).

The biological body imaging system 10 in Embodiment 3 has a numerical aperture (NA) of 0.5, a field of view of 0.5 mm in the object space, telecentricity smaller than 0.2° in the image space, and an operating distance of 2.15 mm.

Figure 20:
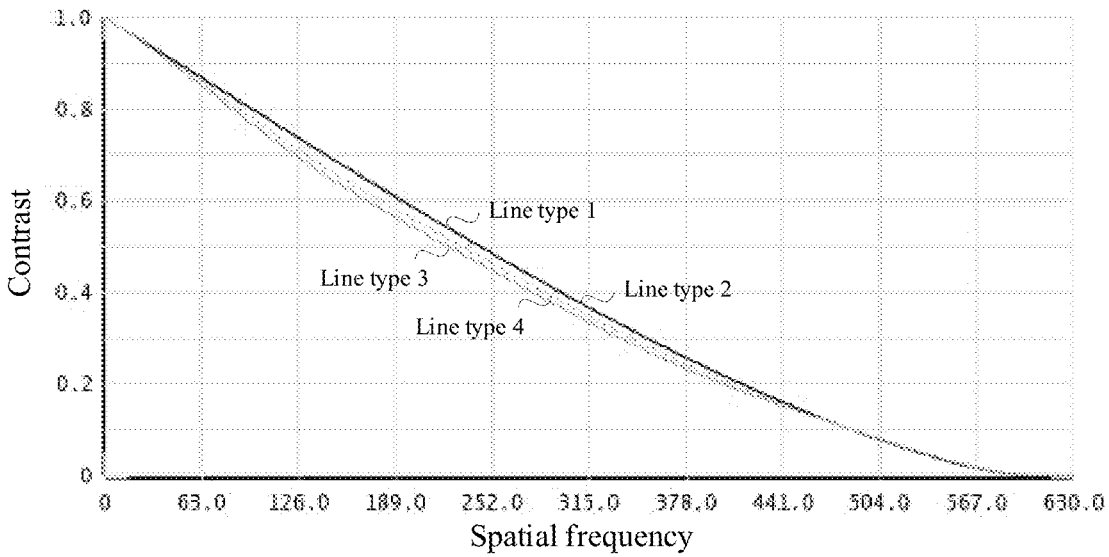
FIG. 20 is an MTF graph of a biological body imaging system at a field of view of 0.707 in a first lens combination manner according to Embodiment 3.
Figure 21:
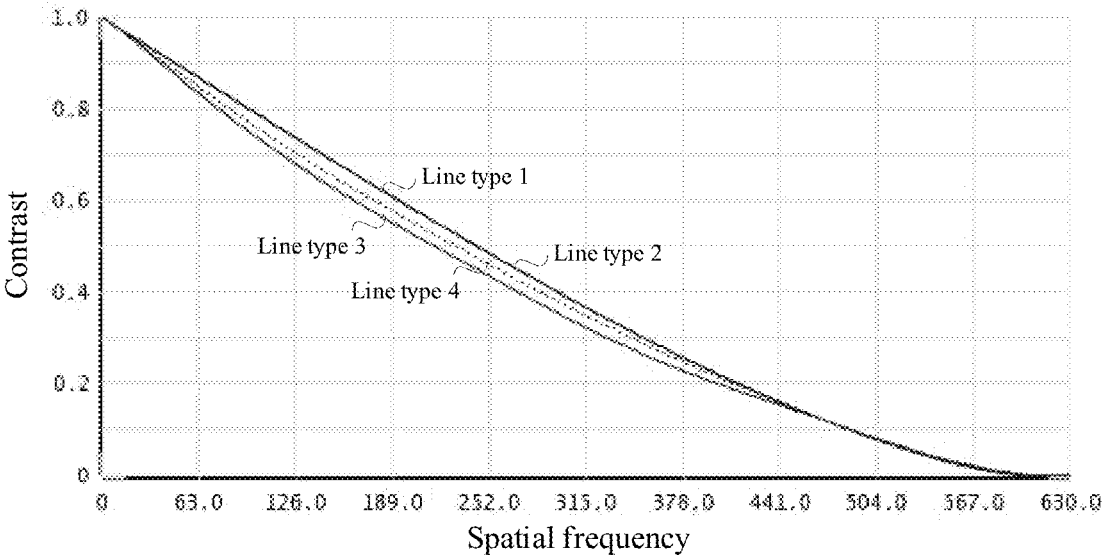
FIG. 21 is an MTF graph of a biological body imaging system at a field of view of 1.0 in a first lens combination manner according to Embodiment 3.
Figure 22:
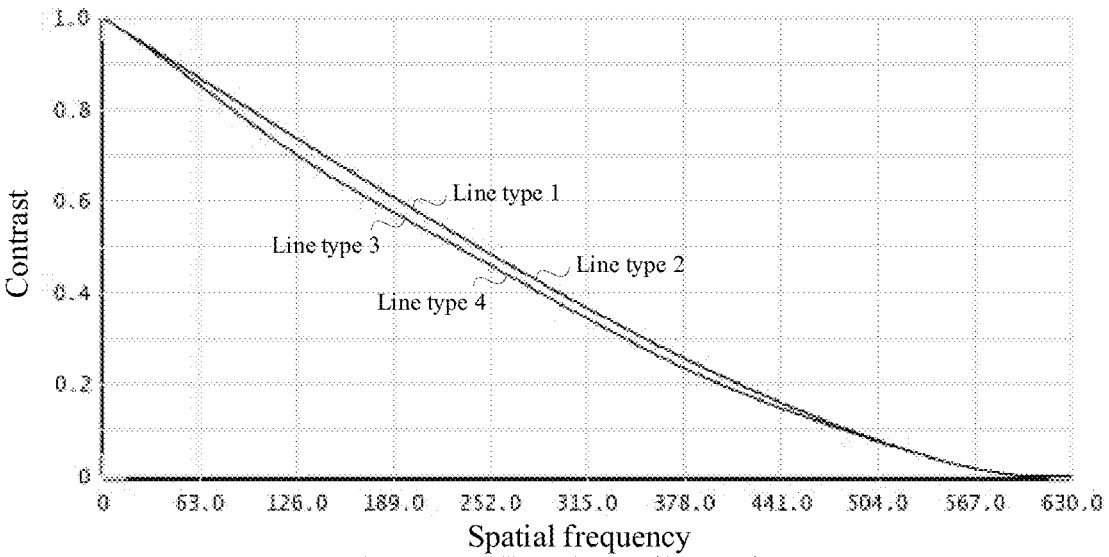
FIG. 22 is an MTF graph of a biological body imaging system at a central field of view in a first lens combination manner according to Embodiment 3.
Figure 23:
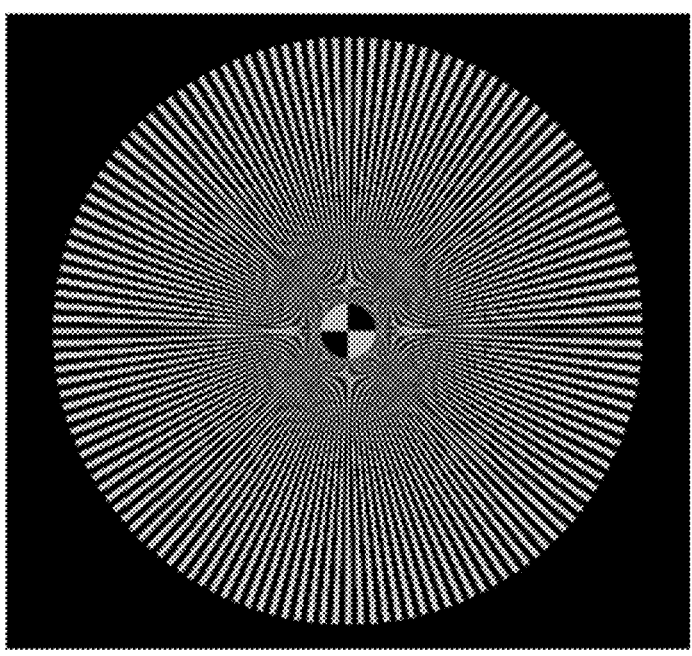
FIG. 23 is a Siemens star chart of a biological body imaging system in a first lens combination manner according to Embodiment 3.

As shown in FIGS. 20 to 22, FIG. 20 is an MTF graph of a biological body imaging system 10 (that is, which is formed by a first lens set 11, a second lens set 12, a third lens set 13, and a fourth lens set 14) at a field of view of 0.707 according to Embodiment 3; FIG. 21 is an MTF graph of a biological body imaging system 10 at a field of view of 1.0 according to Embodiment 3; and FIG. 22 is an MTF graph of a biological body imaging system 10 at a central field of view according to Embodiment 1. Referring to FIG. 23, FIG. 23 is a Siemens star chart of a biological body imaging system 10 (that is, which is formed by a first lens set 11, a second lens set 12, a third lens set 13, and a fourth lens set 14) in a first lens combination manner according to Embodiment 3.

The abscissa in FIG. 20 represents spatial frequency in the unit of cycles per millimeter (cycles/mm). In FIG. 20, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.988963, 0.977883, 0.966706, 0.955349, 0.943742, 0.931908, 0.919885, 0.907686, 0.895322, 0.882814, 0.870187, 0.857467, 0.84468, 0.831857, 0.81903, 0.806228, 0.79348, 0.780815, 0.768257, 0.755832, 0.743558, 0.731448, 0.719512, 0.707768, 0.696227, 0.684867, 0.67367, 0.662667, 0.651902, 0.641439, 0.631304, 0.621373, 0.611517, 0.601746, 0.592091, 0.582544, 0.57308, 0.56365, 0.554225, 0.544861, 0.535626, 0.526532, 0.517561, 0.508615, 0.499606, 0.490544, 0.481463, 0.472368, 0.463248, 0.454058, 0.444777, 0.435507, 0.426349, 0.417277, 0.408235, 0.399186, 0.390098, 0.380939, 0.371711, 0.362552, 0.353578, 0.344694, 0.335798, 0.326987, 0.318367, 0.309883, 0.301457, 0.29308, 0.284754, 0.27644, 0.268129, 0.259978, 0.252115, 0.244399, 0.236695, 0.229145, 0.221891, 0.214786, 0.207682, 0.200725, 0.194057, 0.187521, 0.18096, 0.174518, 0.168339, 0.162261, 0.156118, 0.150056, 0.144217, 0.138439, 0.132559, 0.126717, 0.121058, 0.115426, 0.109668, 0.103922, 0.098328, 0.092733, 0.087008, 0.081407, 0.076157, 0.071015, 0.065714, 0.0604, 0.055249, 0.050164, 0.045054, 0.040099, 0.035468, 0.031004, 0.026564, 0.022389, 0.018708, 0.015309, 0.011967, 0.008822, 0.006049, 0.003586, 0.001439, 0.000128, 0.000016, 0.000327, 0.000253, 0, 0, 0. Actual values (that is, ordinate values) on the Y-axis corresponding to line type 4 (actual transfer function in the sagittal direction) are respectively as follows: 1, 0.989022, 0.978051, 0.967072, 0.95598, 0.944679, 0.933192, 0.921562, 0.909799, 0.897907, 0.885903, 0.873806, 0.861638, 0.849417, 0.837167, 0.824912, 0.812676, 0.800482, 0.788352, 0.776305, 0.764361, 0.752536, 0.740839, 0.729278, 0.717869, 0.706623, 0.695516, 0.684529, 0.673697, 0.663074, 0.652716, 0.642648, 0.632748, 0.622893, 0.613095, 0.603387, 0.593764, 0.584204, 0.574659, 0.565098, 0.55559, 0.546212, 0.53697, 0.527837, 0.518724, 0.509548, 0.50032, 0.491073, 0.481814, 0.472539, 0.463194, 0.453755, 0.444339, 0.435062, 0.425882, 0.416725, 0.407564, 0.398374, 0.389114, 0.379778, 0.37052, 0.361471, 0.352513, 0.343527, 0.334626, 0.325934, 0.317379, 0.30886, 0.300376, 0.291935, 0.283492, 0.275033, 0.266726, 0.258712, 0.250833, 0.242934, 0.235178, 0.227723, 0.220404, 0.213061, 0.205852, 0.198935, 0.192143, 0.185306, 0.178581, 0.172123, 0.165763, 0.159332, 0.152979, 0.146855, 0.140797, 0.134643, 0.128532, 0.122609, 0.116728, 0.110738, 0.104768, 0.098947, 0.093146, 0.087259, 0.081519, 0.076132, 0.070869, 0.065482, 0.060083, 0.054827, 0.049666, 0.044546, 0.039581, 0.034884, 0.03038, 0.025999, 0.021882, 0.018162, 0.014744, 0.011506, 0.008443, 0.005603, 0.003121, 0.001184, 0.000109, 0.000037, 0.000297, 0.000223, 0, 0, 0.

The abscissa in FIG. 21 represents spatial frequency in the unit of cycles per millimeter (cycles/mm). In FIG. 21, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.988465, 0.976517, 0.963856, 0.950633, 0.937084, 0.923348, 0.909535, 0.895737, 0.882026, 0.868414, 0.854905, 0.841532, 0.828323, 0.81526, 0.802326, 0.789544, 0.776935, 0.764486, 0.752181, 0.740037, 0.728071, 0.716272, 0.704626, 0.693147, 0.681845, 0.670704, 0.659704, 0.648844, 0.638148, 0.627713, 0.617606, 0.607693, 0.597833, 0.588033, 0.578331, 0.568715, 0.55916, 0.549642, 0.54014, 0.530662, 0.521237, 0.511941, 0.502822, 0.493757, 0.484618, 0.475428, 0.466233, 0.457032, 0.447812, 0.438555, 0.429253, 0.419949, 0.410699, 0.401565, 0.392582, 0.383665, 0.374725, 0.365766, 0.356825, 0.347963, 0.339238, 0.330673, 0.322273, 0.31401, 0.305867, 0.297901, 0.290155, 0.282557, 0.275021, 0.267537, 0.260128, 0.252863, 0.245803, 0.238922, 0.232183, 0.225591, 0.219155, 0.212851, 0.206656, 0.200576, 0.194612, 0.188731, 0.1829, 0.177131, 0.171434, 0.165765, 0.160082, 0.154408, 0.148766, 0.143106, 0.137382, 0.131635, 0.125903, 0.120135, 0.114283, 0.10842, 0.102611, 0.096771, 0.090839, 0.084982, 0.079362, 0.073886, 0.068442, 0.0631, 0.057933, 0.05283, 0.047711, 0.042805, 0.038303, 0.033948, 0.029513, 0.025351, 0.02178, 0.018416, 0.014893, 0.011644, 0.009056, 0.006541, 0.003624, 0.001249, 0.000333, 0.000256, 0.000202, 0.000099, 0.000034, 0. Actual values (that is, ordinate values) on the Y-axis corresponding to line type 4 (actual transfer function in the sagittal direction) are respectively as follows: 1, 0.988684, 0.977182, 0.965353, 0.953247, 0.940955, 0.928565, 0.916153, 0.903772, 0.891459, 0.879214, 0.867038, 0.854949, 0.842964, 0.831066, 0.819236, 0.807491, 0.79585, 0.784299, 0.772822, 0.761436, 0.750161, 0.738983, 0.72789, 0.716902, 0.706037, 0.695264, 0.684559, 0.673956, 0.663508, 0.653283, 0.643316, 0.63349, 0.623681, 0.613903, 0.604194, 0.594553, 0.584964, 0.575387, 0.565795, 0.556248, 0.546817, 0.537531, 0.528384, 0.519278, 0.510119, 0.500925, 0.491735, 0.482556, 0.473379, 0.464161, 0.454883, 0.445644, 0.436543, 0.427568, 0.418677, 0.409817, 0.400937, 0.39201, 0.383044, 0.374166, 0.365483, 0.356914, 0.348367, 0.339913, 0.331632, 0.323487, 0.315416, 0.307383, 0.29936, 0.291306, 0.28322, 0.275248, 0.26751, 0.25987, 0.252195, 0.244616, 0.237258, 0.229982, 0.222647, 0.215391, 0.208349, 0.201368, 0.194297, 0.187284, 0.180476, 0.173709, 0.166824, 0.15998, 0.153335, 0.146721, 0.139975, 0.133264, 0.12676, 0.120294, 0.113703, 0.107166, 0.100859, 0.0946, 0.088231, 0.082061, 0.076374, 0.070891, 0.06531, 0.059799, 0.054557, 0.049437, 0.044302, 0.039385, 0.034897, 0.030593, 0.026251, 0.022187, 0.0187, 0.015471, 0.012174, 0.009059, 0.006402, 0.003981, 0.001662, 0.000148, 0, 0.00035, 0.000276, 0, 0, 0.

The abscissa in FIG. 22 represents spatial frequency in the unit of cycles per millimeter (cycles/mm). In FIG. 22, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.989005, 0.977998, 0.966945, 0.95574, 0.944284, 0.932604, 0.920747, 0.908728, 0.896555, 0.884257, 0.871864, 0.859404, 0.846903, 0.834392, 0.821903, 0.809462, 0.797097, 0.78483, 0.772684, 0.760678, 0.748828, 0.73714, 0.72562, 0.714283, 0.703137, 0.692154, 0.68131, 0.670642, 0.6602, 0.650036, 0.640168, 0.630473, 0.620829, 0.611243, 0.601747, 0.592334, 0.582981, 0.573637, 0.564269, 0.554947, 0.545751, 0.536681, 0.527705, 0.518734, 0.509688, 0.500578, 0.491433, 0.482263, 0.47306, 0.463771, 0.454371, 0.44498, 0.435715, 0.426527, 0.417341, 0.40813, 0.398874, 0.389531, 0.380094, 0.37072, 0.361544, 0.352442, 0.343289, 0.334209, 0.325334, 0.316585, 0.307854, 0.299148, 0.290483, 0.281816, 0.273132, 0.264605, 0.256377, 0.24829, 0.240189, 0.232242, 0.224612, 0.217136, 0.20965, 0.202316, 0.195298, 0.188427, 0.181535, 0.174777, 0.168309, 0.161965, 0.155578, 0.149291, 0.143252, 0.137301, 0.131281, 0.125321, 0.119557, 0.11385, 0.108056, 0.102286, 0.096656, 0.091054, 0.085385, 0.079857, 0.074655, 0.069565, 0.064351, 0.059108, 0.053974, 0.048926, 0.043929, 0.039067, 0.034423, 0.029964, 0.025662, 0.021608, 0.017894, 0.01448, 0.011296, 0.008276, 0.005411, 0.002924, 0.001084, 0.000112, 0.000051, 0.000281, 0.000207, 0, 0, 0. Actual values (that is, ordinate values) on the Y-axis corresponding to line type 4 (actual transfer function in the sagittal direction) are respectively as follows: 1, 0.989005, 0.977998, 0.966945, 0.95574, 0.944284, 0.932604, 0.920747, 0.908728, 0.896555, 0.884257, 0.871864, 0.859404, 0.846903, 0.834392, 0.821903, 0.809462, 0.797097, 0.78483, 0.772684, 0.760678, 0.748828, 0.73714, 0.72562, 0.714283, 0.703137, 0.692154, 0.68131, 0.670642, 0.6602, 0.650036, 0.640168, 0.630473, 0.620829, 0.611243, 0.601747, 0.592334, 0.582981, 0.573637, 0.564269, 0.554947, 0.545751, 0.536681, 0.527705, 0.518734, 0.509688, 0.500578, 0.491433, 0.482263, 0.47306, 0.463771, 0.454371, 0.44498, 0.435715, 0.426527, 0.417341, 0.40813, 0.398874, 0.389531, 0.380094, 0.37072, 0.361544, 0.352442, 0.343289, 0.334209, 0.325334, 0.316585, 0.307854, 0.299148, 0.290483, 0.281816, 0.273132, 0.264605, 0.256377, 0.24829, 0.240189, 0.232242, 0.224612, 0.217136, 0.20965, 0.202316, 0.195298, 0.188427, 0.181535, 0.174777, 0.168309, 0.161965, 0.155578, 0.149291, 0.143252, 0.137301, 0.131281, 0.125321, 0.119557, 0.11385, 0.108056, 0.102286, 0.096656, 0.091054, 0.085385, 0.079857, 0.074655, 0.069565, 0.064351, 0.059108, 0.053974, 0.048926, 0.043929, 0.039067, 0.034423, 0.029964, 0.025662, 0.021608, 0.017894, 0.01448, 0.011296, 0.008276, 0.005411, 0.002924, 0.001084, 0.000112, 0.000051, 0.000281, 0.000207, 0, 0, 0.

It should be noted that in FIGS. 20 to 22, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction.

It can be known from FIGS. 20 to 22 that in the ideal state, optimal imaging effect with low distortion can be achieved when the transfer function in the tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

Based on the same invention concept, the present invention further discloses an optical inspection device. The optical inspection device includes the biological body imaging system as described above. The biological body imaging system 10 may be mounted on an inner side of the optical inspection device, to optically image tissue of the biological body (which includes a living creature or a detached biological tissue), thus allowing the operator (for example, medical personnel or scientific researcher) to observe the image of the biological body. For details, references may be made to the foregoing description, and details are not repeated.

The series of detailed descriptions listed in the preceding text are only specific explanations for the feasible implementations of the present invention. They are not intended to limit the protection scope of the present invention. Equivalent implementations or modifications made within the spirit of the technical concept of the present invention should be included in the protection scope of the present invention.

For those skilled in the art, it is apparent that the present invention is not limited to the details of the exemplary embodiments mentioned above. Moreover, the present invention can be implemented in other specific forms without departing from the spirit or basic feature of the present invention. Therefore, from any perspective, the embodiments should be regarded as exemplary and non-limiting. The scope of the present invention is defined by the appended claims rather than the above description. Therefore, it is intended to encompass all changes in the meaning and scope of the equivalent elements of the claims within the present invention. Any reference signs in the claims should not be construed as limitation on the related claims.

Additionally, it should be understood that though this specification is described according to the implementations, not every implementation merely includes a single independent technical solution. This manner of description in the specification is solely for clarity. Those skilled in the art should consider the specification as a whole, and the technical solutions in various embodiments can also be appropriately combined to form other implementations understandable by those skilled in the art.

What is claimed is:

1. A biological body imaging system, comprising:
a first lens set with a positive focal power, a second lens set with a positive focal power, a third lens set with a positive focal power, and a fourth lens set with a positive focal power that are sequentially arranged from an object side along a same optical axis; wherein
the first lens set comprises a second lens with a plane facing the object side and a convex surface facing an image side, and a third lens with a convex surface facing the object side and a convex surface facing the image side, the second lens set comprises a fourth lens, having a negative focal power, with a convex surface facing the object side and a concave surface facing the image side, and a fifth lens with a convex surface facing the object side and a convex surface facing the image side that fit with each other, the third lens set comprises a sixth lens with a convex surface facing the object side and a concave surface facing the image side, and the fourth lens set comprises a seventh lens, having a negative focal power, with a concave surface facing the object side and a convex surface facing the image side and an eighth lens, having a positive focal power, with a convex surface facing the object side and a concave surface facing the image side; wherein
there are seven lens having a focal power, a combined focal length $f_1$ of the first lens set and a conjugate distance T satisfy $0.15 \leq f_1/T \leq 0.18$, a combined focal length $f_4$ of the fourth lens set and the combined focal length $f_1$ of the first lens set satisfy $1.8 \leq f_4/f_1 \leq 2.2$, and a focal length $f_{41}$ of the seventh lens and a focal length $f_{42}$ of the eighth lens satisfy $-1 \leq f_{42}/f_{41} \leq -0.8$.

2. The biological body imaging system according to claim 1, wherein the first lens set further comprises a first lens disposed on an object side of the second lens along the same optical axis and having a plane facing the object side.

3. The biological body imaging system according to claim 2, wherein the first lens fits with the second lens, and surfaces of the first lens on the object side and the image side both form planes.

4. The biological body imaging system according to claim 1, wherein a curvature radius $r_4$ corresponding to the surface of the third lens facing the object side, an operating distance H of the biological body imaging system, and an air gap $H_1$ between the second lens and the third lens satisfy $4.75 \leq r_4/(H+H_1) \leq 15.9$; wherein
the operating distance H refers to a distance corresponding to a gap between a central position of the surface of the second lens facing the object side and a biological body, and the air gap $H_1$ refers to a distance corresponding to a gap between a central position of the second lens and a central position of the third lens.

5. The biological body imaging system according to claim 1, wherein the combined focal length $f_1$ of the first lens set and a combined focal length $f_2$ of the second lens set satisfy $7 \leq f_2/f_1 \leq 11.5$.

6. The biological body imaging system according to claim 1, wherein a combined focal length $f_2$ of the second lens set and a combined focal length $f_3$ of the third lens set satisfy $2.2 \leq f_2/f_3 \leq 4.5$.

7. The biological body imaging system according to claim 1, wherein a curvature radius $r_3$ corresponding to the surface of the second lens facing the image side and a focal length $f_{12}$ of the second lens satisfy $-0.91 \leq r_3/f_{12} \leq -0.81$.

8. The biological body imaging system according to claim 1, wherein a curvature radius $r_9$ corresponding to the surface of the sixth lens facing the object side and a combined focal length $f_3$ of the third lens set satisfy $0.15 \leq r_9/f_3 \leq 0.35$.

9. The biological body imaging system according to claim 1, wherein a curvature radius $r_{12}$ corresponding to the surface of the seventh lens facing the image side and a curvature radius $r_{13}$ corresponding to the surface of the eighth lens facing the object side satisfy $-0.7 \leq r_{12}/r_{13} \leq -0.5$.

10. The biological body imaging system according to claim 1, wherein a central thickness $D_9$ of the sixth lens and the conjugate distance T satisfy $0.13 \leq D_9/T$.

11. An optical inspection device, wherein
the optical inspection device comprises the biological body imaging system according to any one of claims 1 to 10.

* * * * *